United States Patent [19]
Wu et al.

[11] Patent Number: 6,117,901
[45] Date of Patent: Sep. 12, 2000

[54] N-(ARYL/HETEROARYLACETYL) AMINO ACID ESTERS, PHARMACEUTICAL COMPOSITIONS COMPRISING SAME, AND METHODS FOR USE

[75] Inventors: Jing Wu, San Mateo; Eugene D. Thorsett, Moss Beach, both of Calif.; Jeffrey S. Nissen; Thomas E. Mabry, both of Indianapolis, Ind.; Lee H. Latimer, Oakland, Calif.; Varghese John, San Francisco, Calif.; Lawrence Y. Fang, Foster City, Calif.; James E. Audia, Indianapolis, Ind.

[73] Assignees: Athena Neurosciences, Inc., South San Francisco, Calif.; Eli Lilly & Company, Indianapolis, Ind.

[21] Appl. No.: 08/976,179

[22] Filed: Nov. 21, 1997

Related U.S. Application Data
[60] Provisional application No. 60/098,551, Nov. 22, 1996.

[51] Int. Cl.$^7$ ................................................. A61K 31/16
[52] U.S. Cl. ............................................................ 514/513
[58] Field of Search ............................................. 514/513

[56] References Cited

U.S. PATENT DOCUMENTS

| | | | |
|---|---|---|---|
| 3,657,341 | 4/1972 | Thorne | 514/513 |
| 3,876,683 | 4/1975 | Vincent et al. | 514/513 |
| 4,666,829 | 5/1987 | Glenner et al. | 435/6 |

FOREIGN PATENT DOCUMENTS

| | | |
|---|---|---|
| 860336 | 1/1971 | Canada . |
| 0652009 | 5/1995 | European Pat. Off. . |
| 0778266 | 6/1997 | European Pat. Off. . |
| 95/09838 | 4/1995 | WIPO . |
| 96/22966 | 8/1996 | WIPO . |
| 96/39194 | 12/1996 | WIPO . |
| WO 96/39194 | 12/1996 | WIPO . |

OTHER PUBLICATIONS

Doherty, et al., The Resolution of Amino Acids by Asymmetric Enzymatic Synthesis, J. Biol. Chem., 189:447–454 (1951).

Pazhanisamy, et al., β–Lactamase–Catalyzed Amnolysis of Depsipeptides: Peptide Inhibition and a New Kinetic Mechanism, Biochemistry, 28:6875–6882 (1989).

Ogawa, et al., A New Method for Preparing D–Penicillamine, Reaction of Benzylpenicilloic Acid α–Amides with Arylamines, Chem. Pharm. Bull., 36(6):1957–1962 (1988).

Cordell, β–Amyloid Formation as a Potential Therapeutic Target for Alzheimer's Disease, Ann. Rev. Pharmacol. Toxicol., 34:69–89 (1994).

Smith, et al., *β–APP Processing as a Therapeutic Target for Alzheimer's Disease*, 3:439–445 (1997).

Clark, "The Chemistry of Penicillin", Princeton University Press, pp. 240, 708, 786, 795 and 875 (1949).

Papadopoulos, et al., "Anodic Oxidation of N–Acyl and N–Alkoxycarbonyl Dipeptide Esters as a Key Step for the Formulation of Chiral Heterocyclic Synthetic Building Blocks", Tetrahedron, 47(4/5):563–572 (1991).

Waldmann, et al., "Selective Enzymatic Removal of Protecting Groups: The Phenylacetamide as Amino Protecting Group in Phosphopeptide Synthesis", Tetrahedron letters, 37(48):8725–8728 (1996).

Pessina, et al., "Amide–Bond Syntheses Catalyzed by Penicillin Acylase", Helvetica Chimica Acta, 71:631–641 (1988).

Cordell, Barbara, "β–Amyloid Formation as a Potential Therapeutic Target for Alzheimer's Disease", Annu. Rev. Pharmacol. Toxicol. 34, pp. 69–89 (1994).

Smith, et al., "β–APP Processing as a Therapeutic Target for Alzheimer's Disease", Current Pharmaceutical Design, 3(4), pp. 439–445 (1997).

*Primary Examiner*—Zinna Northington Davis
*Attorney, Agent, or Firm*—Burns, Doane, Swecker & Mathis, LLC

[57] ABSTRACT

Disclosed are compounds which inhibit β-amyloid peptide release and/or its synthesis, and, accordingly, have utility in treating Alzheimer's disease. Also disclosed pharmaceutical compositions comprising a compound which inhibits β-amyloid peptide release and/or its synthesis as well as methods for treating Alzheimer's disease both prophylactically and therapeutically with such pharmaceutical compositions.

23 Claims, No Drawings

N-(ARYL/HETEROARYLACETYL) AMINO ACID ESTERS, PHARMACEUTICAL COMPOSITIONS COMPRISING SAME, AND METHODS FOR USE

CROSS-REFERENCE TO RELATED APPLICATIONS

This application claims the benefit of U.S. Provisional Application No. 60/098,551, which was converted pursuant to 37 C.F.R. §1.53(b)(2)(ii) from U.S. patent application Ser. No. 08/754,895, file Nov. 22, 1996 which is incorporated herein by reference in its entirety.

BACKGROUND OF THE INVENTION

1. Field of the Invention

This invention relates to compounds which inhibit β-amyloid peptide release and/or its synthesis, and, accordingly, have utility in treating Alzheimer's disease. This invention also relates to pharmaceutical compositions comprising such compounds as well as methods for inhibiting release of β-amyloid peptide.

REFERENCES

The following publications, patents and patent applications are cited in this application as superscript numbers:

[1] Glenner, et al., "Alzheimer's Disease: Initial Report of the Purification and Characterization of a Novel Cerebrovascular Amyloid Protein", *Biochem. Biophys. Res. Commun.*, 120:885–890 (1984).

[2] Glenner, et al., "Polypeptide Marker for Alzheimer's Disease and its Use for Diagnosis", *U.S. Pat. No. 4,666,829* issued May 19, 1987.

[3] Selkoe, "The Molecular Pathology of Alzheimer's Disease", *Neuron*, 6:487–498 (1991).

[4] Goate, et al., "Segregation of a Missense Mutation in the Amyloid Precursor Protein Gene with Familial Alzheimer's Disease", *Nature*, 349:704–706 (1990).

[5] Chartier-Harlan, et al., "Early-Onset Alzheimer's Disease Caused by Mutations at Codon 717 of the β-Amyloid Precursor Proteing Gene", *Nature*, 353:844–846 (1989).

[6] Murrell, et al., "A Mutation in the Amyloid Precursor Protein Associated with Hereditary Alzheimer's Disease", *Science*, 254:97–99 (1991).

[7] Mullan, et al., "A Pathogenic Mutation for Probable Alzheimer's Disease in the APP Gene at the N-Terminus of β-Amyloid", *Nature Genet.*, 1:345–347 (1992).

[8] Schenk, et al., "Methods and Compositions for the Detection of Soluble β-Amyloid Peptide", *International Patent Application Publication No. WO 94/10569*, published May 11, 1994.

[9] Selkoe, "Amyloid Protein and Alzheimer's Disease", *Scientific American*, pp. 2–8, November, 1991.

[10] Losse, et al., Tetrahedron, 27:1423–1434 (1971).

[11] Citron, et al., "Mutation of the β-Amyloid Precursor Protein in Familial Alzheimer's Disease Increases β-Protein Production", *Nature*, 360:672–674 (1992).

[12] Hansen, et al., "Reexamination and Further Development of a Precise and Rapid Dye Method for Measuring Cell Growth/Cell Kill", *J. Immun. Meth.*, 119:203–210 (1989).

[13] P. Seubert, *Nature* (1992) 359:325–327

[14] Johnson-Wood et al., *PNAS USA* (1997) 94:1550–1555

[15] *Tetrahedron Letters*, 34(48), 7685 (1993))

All of the above publications, patents and patent applications are herein incorporated by reference in their entirety to the same extent as if each individual publication, patent or patent application was specifically and individually indicated to be incorporated by reference in its entirety.

STATE OF THE ART

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829.[2]

Molecular biological and protein chemical analyses have shown that the β-amyloid peptide is a small fragment of a much larger precursor protein (APP), that is normally produced by cells in many tissues of various animals, including humans. Knowledge of the structure of the gene encoding the APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier-Harlan, et al.[5]; and Murrell, et al.[6]) and is referred to as the Swedish variant. A double mutation changing lysine[595]-methionine[596] to asparagine[595]-leucine[596] (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

SUMMARY OF THE INVENTION

This invention is directed to the discovery of a class of compounds which inhibit β-amyloid peptide release and/or its synthesis and, therefore, are useful in the prevention of AD in patients susceptible to AD and/or in the treatment of patients with AD in order to inhibit further deterioration in their condition. The class of compounds having the described properties are defined by formula I below:

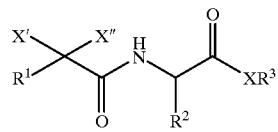

I wherein $R^1$ is selected from the group consisting of a) alkyl, alkenyl, alkcycloalkyl, phenyl—$(R)_m$—, naphthyl—$(R)_m$— wherein R is an alkylene group of from 1 to 8 carbon atoms and m is an integer equal to 0 or 1, cycloalkyl, cycloalkenyl, 3-pyridyl, 4-pyridyl and heteroaryl, other than 3- and 4-pyridyl, of 3 to 10 atoms and 1 to 4 heteroatoms selected from oxygen, sulfur and nitrogen wherein the heteroaryl group is optionally substituted with 1 to 3 substituents selected from the group consisting of alkyl, alkoxy, aryl, aryloxy, halo, nitro, thioalkoxy, and thioaryloxy with the proviso that for such heteroaryls when there is at least one nitrogen heteroatom, there is also at least one oxygen and/or sulfur heteroatom;

(b) a substituted phenyl group of formula II:

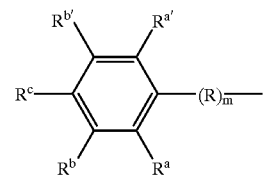

II wherein R is alkylene of from 1 to 8 carbon atoms,
m is an integer equal to 0 or 1,
$R^a$ and $R^{a'}$ are independently selected from the group consisting of hydrogen, hydroxy, fluoro and methyl;
$R^b$ and $R^{b'}$ are independently selected from the group consisting of hydrogen, alkyl, alkoxy, aryl, cyano, cycloalkyl, halo, heteroaryl, heterocyclic, nitro, trihalomethyl, thioalkoxy, thioaryloxy, thioheteroaryloxy, and —C(O)$R^4$ where $R^4$ is selected from the group consisting of alkyl, aryl, alkoxy and aryloxy; and
$R^c$ is selected from the group consisting of hydrogen, alkyl, aryl, cyano, halo, nitro, and where $R^b$ and $R^c$ are fused to form a methylenedioxy ring with the phenyl ring; and
when $R^b$ and/or $R^{b'}$ and/or $R^c$ is fluoro, chloro, bromo and/or nitro, then $R^a$ and/or $R^{a'}$ can also be chloro; and (c) 1- or 2-naphthyl—$(R)_m$— substituted at the 5, 6, 7 and/or 8 positions with 1 to 4 substituents selected from the group consisting alkyl, alkoxy, halo, cyano, nitro, trihalomethyl, and thioalkoxy wherein R is an alkylene group of from 1 to 8 carbon atoms and m is an integer equal to 0 or 1;

$R^2$ is selected from the group consisting of hydrogen, alkyl, phenyl, alkylalkoxy, alkylthioalkoxy; and
$R^3$ is selected from the group consisting of —(CH$_2$)$_n$CR$^{10}$R$^5$R$^6$ wherein n is an integer equal to 0, 1 or 2, $R^5$ and $R^6$ are independently selected from hydrogen, alkyl, alkenyl, aryl, heteroaryl, heterocyclic, —NR$^7$R$^8$ where $R^7$ and $R^8$ are independently hydrogen or alkyl and —COOR$^9$ where $R^9$ is alkyl, and further wherein $R^5$ and $R^6$ can be joined to form a cycloalkyl group, a cycloalkenyl group, an aryl group, a heteroaryl group, and a heterocyclic group, and when $R^5$ and $R^6$ do not join to form an aryl or heteroaryl group, then $R^{10}$ is selected from hydrogen and alkyl with the proviso that when n is zero, then $R^{10}$ is hydrogen and when n is greater than zero and $R^5$ and $R^6$ are joined to form an aryl or heteroaryl group, then $R^{10}$ becomes a bond within that group;
X is oxygen or sulfur;
X' is hydrogen, hydroxy or fluoro;
X" is hydrogen, hydroxy or fluoro, or X' and X" together form an oxo group, and
pharmaceutically acceptable salts thereof
with the provisos that:
when $R^1$ is phenyl, $R^2$ is —CH(CH$_3$)CH$_2$CH$_3$, X is oxygen, and X' and X" are hydrogen, then $R^3$ is not —CH$_2$CH$_3$ or —CH$_2$CH(CH$_3$)$_2$
when $R^1$ is phenyl, $R^3$ is —CH$_2$CH(CH$_3$)$_2$, X is oxygen, and X' and X" are hydrogen, then $R^2$ is not —CH(CH$_3$)$_2$
when $R^1$ is pyrid-3-yl, $R^2$ is ethyl, X is oxygen, and X' and X" are hydrogen, then $R^3$ is not —CH$_2$CH(CH$_3$)$_2$,
when $R^1$ is indoxazin-3-yl, 2,4-dimethylthiazol-5-yl, 4-methyl-1,2,5-thiooxadizol-3-yl or 3,5-di(trifluoromethyl)phenyl, $R^2$ is methyl, X is oxygen, and X' and X" are hydrogen, then $R^3$ is not —CH$_2$CH(CH$_3$)$_2$, and
when $R^1$ is —CH$^2$-phenyl, $R^3$ is —CH$_2$CH$_3$, X is oxygen, and X' and X" are hydrogen, then $R^2$ is not —CH$_2$CH(CH$_3$)$_2$.

Surprisingly, the substituents at the 2 and/or 6 positions of the phenyl group are limited to those recited above and larger substituents, other than those specifically specified above, eliminate the ability of the resulting compounds to inhibit β-amyloid peptide release and/or its synthesis.

Accordingly, in one of its method aspects, this invention is directed to a method for inhibiting β-amyloid peptide release and/or its synthesis in a cell which method comprises administering to such a cell an amount of a compound or a mixture of compounds of formula I above effective in inhibiting the cellular release and/or synthesis of β-amyloid peptide.

Because the in vivo generation of β-amyloid peptide is associated with the pathogenesis of AD[8,9], the compounds of formula I can also be employed in conjunction with a pharmaceutical composition to prophylactically and/or therapeutically prevent and/or treat AD. Accordingly, in another of its method aspects, this invention is directed to a prophylactic method for preventing the onset of AD in a patient at risk for developing AD which method comprises administering to said patient a pharmaceutical composition comprising a pharmaceutically inert carrier and an effective amount of a compound or a mixture of compounds of formula I above.

In yet another of its method aspects, this invention is directed to a therapeutic method for treating a patient with AD in order to inhibit further deterioration in the condition of that patient which method comprises administering to said patient a pharmaceutical composition comprising a pharmaceutically inert carrier and an effective amount of a compound or a mixture of compounds of formula I above.

In formula I above, preferred $R^1$ unsubstituted aryl groups include, for example, phenyl, 1-naphthyl, 2-naphthyl, and the like.

Preferred $R^1$ substituted aryl groups include, for example, monosubstituted phenyls having a single substitution at the 2, 3 or 4 positions where each of the particular substituents is governed by the respective $R^a/R^{a'}$, $R^b/R^{b'}$ and $R^c$ groups; disubstituted phenyls which include those having two substituents at the 2,3-positions, 2,4-positions, 2,5-positions, 2,6-positions, 3,4-positions, 3,5-positions or 3,6-positions where each of these substituents is governed by the respective $R^a$, $R^{a'}$, $R^b$, $R^{b'}$ and $R^c$ groups; and trisubstituted phenyls which include those having three substituents at the 2,3,4-positions, 2,3,5-positions, 2,3,6-positions, 3,4,5-positions and 3,4,6-positions again where each of these substituents is governed by the respective $R^a$, $R^{a'}$, $R^b$, $R^{b'}$ and $R^c$ groups. Preferably, the substituted phenyl groups do not include more than 3 substituents.

Examples of substituted phenyls include, for instance, 4-fluorophenyl, 4-chlorophenyl, 4-bromophenyl, 4-nitrophenyl, 4-methylphenyl, 3-methoxyphenyl, 3-nitrophenyl, 3-fluorophenyl, 3-chlorophenyl, 3-bromophenyl, 3-thiomethoxyphenyl, 3-methylphenyl, 3-trifluoromethylphenyl, 2-hydroxyphenyl, 2-methylphenyl, 2-fluorophenyl, 3,4-dichlorophenyl, 3,4-methylenedioxyphenyl, 3,5-difluorophenyl, 3,5-dichlorophenyl, 2,4-dichlorophenyl, and 2,5-difluorophenyl.

Preferred $R^1$ groups represented by phenyl—R— include, by way of example, benzyl, 3-phenylethyl, 4-phenyl-n-propyl, and the like.

Preferred $R^1$ alkyl, alkcycloalkyl, cycloalkyl and cycloalkenyl groups include, by way of example, sec-butyl, cyclopropyl, cyclobutyl, cyclohexyl, cyclopentyl, cyclohex-1-enyl, —$CH_2$-cyclopropyl, —$CH_2$-cyclobutyl, —$CH_2$-cyclohexyl, —$CH_2$-cyclopentyl, —$CH_2CH_2$-cyclopropyl, —$CH_2CH_2$-cyclobutyl, —$CH_2CH_2$-cyclohexyl, —$CH_2CH_2$-cyclopentyl, and the like.

Preferred $R^1$ heteroaryls and substituted heteroaryls include, by way of example, pyrid-3-yl, pyrid-4-yl, thien-2-yl, thien-3-yl, benzothiazol-4-yl, 2-phenylbenzoxazol-5-yl, furan-2-yl, benzofuran-2-yl, benzothiophen-3-yl, 2-chlorothien-5-yl, 3-methylisoxazol-5-yl, 2-(phenylthio)thien-5-yl, 6-methoxythiophen-2-yl, 3-phenyl-1,2,4-thiooxadiazol-5-yl, 2-phenyloxazol-4-yl, and the like.

Preferably $R^2$ is selected from the group consisting of alkyl of from 1 to 4 carbon atoms, phenyl, alkylalkoxy of from 1 to 4 carbon atoms and alkylthioalkoxy of from 1 to 4 carbon atoms. Particularly preferred $R^2$ substituents include, by way of example, methyl, ethyl, n-propyl, iso-propyl, n-butyl, iso-butyl, —$CH_2CH_2SCH_3$, cyclohexyl and phenyl.

When X is oxygen, preferred $R^3$ substituents include, for example, methyl, ethyl, iso-propyl, n-propyl, n-butyl, iso-butyl, cyclopentyl, allyl, iso-but-2-enyl, 3-methylpentyl, —$CH_2$-cyclopropyl, —$CH_2$-cyclohexyl, —$CH_2$-(3-tetrahydrofuranyl), —$CH_2$-thien-2-yl, —$CH_2$(1-methyl)cyclopropyl, —$CH_2$-thien-3-yl, —$CH_2$—C(O)O-t-butyl, —$CH_2$-C($CH_3$)$_3$, —$CH_2CH(CH_2CH_3)_2$, -2-methylcyclopentyl, -cyclohex-2-enyl, —$CH[CH(CH_3)_2]$COOCH$_3$, —$CH_2CH_2N(CH_3)_2$, —$CH_2C(CH_3)$=$CH_2$, —$CH_2CH$=$C(CH_3)_2$ and the like.

When X is sulfur, preferred $R^3$ substituents include, for example, iso-but-2-enyl and iso-butyl.

This invention also provides for novel pharmaceutical compositions comprising a pharmaceutically inert carrier and a compound of the formula I above.

Particularly preferred compounds for use in the methods and compositions of this invention include, by way of example, the following wherein the stereochemistry of the $R^2$ group (where appropriate) is preferably derived from the L-amino acid:

N-(phenylacetyl)alanine iso-butyl ester
N-(3-phenylpropionyl)alanine iso-butyl ester
N-(3-methylpentanoyl)alanine iso-butyl ester
N-[(4-chlorophenyl)acetyl]alanine iso-butyl ester
N-[(3,4-dichlorophenyl)acetyl]alanine iso-butyl ester
N-[(3-pyridyl)acetyl]alanine iso-butyl ester
N-[(1-naphthyl)acetyl]alanine iso-butyl ester
N-[(2-naphthyl)acetyl]alanine iso-butyl ester
N-(4-phenylbutanoyl)alanine iso-butyl ester
N-(5-phenylpentanoyl)alanine iso-butyl ester
N-[(4-pyridyl)acetyl]alanine iso-butyl ester
2-[(3,4-dichlorophenyl)acetamido]butyric acid iso-butyl ester
2-[(3-methoxyphenyl)acetamido]butyric acid iso-butyl ester
2-[(4-nitrophenyl)acetamido]butyric acid iso-butyl ester
2-[(3,4-methylenedioxyphenyl)acetamido]butyric acid iso-butyl ester
2-[(thien-3-yl)acetamido]butyric acid iso-butyl ester
2-[(4-chlorophenyl)acetamido]butyric acid iso-butyl ester
2-[(3-nitrophenyl)acetamido]butyric acid iso-butyl ester
2-[(2-hydroxyphenyl)acetamido]butyric acid iso-butyl ester
2-[(2-naphthyl)acetamido]butyric acid iso-butyl ester
2-[(2,4-dichlorophenyl)acetamido]butyric acid iso-butyl ester
2-[(4-bromophenyl)acetamido]butyric acid iso-butyl ester
2-[(3-chlorophenyl)acetamido]butyric acid iso-butyl ester
2-[(3-fluorophenyl)acetamido]butyric acid iso-butyl ester
2-[(benzothiazo-4-yl)acetamido]butyric acid iso-butyl ester
2-[(2-methylphenyl)acetamido]butyric acid iso-butyl ester
2-[(2-fluorophenyl)acetamido]butyric acid iso-butyl ester
2-[(4-fluorophen yl)acetamido]butyric acid iso-butyl ester
2-[(3-bromophenyl)acetamido]butyric acid iso-butyl ester
2-[(3-trifluoromethylphenyl)acetamido]butyric acid iso-butyl ester b 2-[(2-thienyl)acetamido]butyric acid iso-butyl ester
2-(phenylacetamido)butyric acid iso-butyl ester
N-(phenylacetyl)valine 2-methylbutyl ester
N-(phenylacetyl)methionine iso-butyl ester
N-(phenylacetyl)leucine iso-butyl ester
N-[(3-chlorophenyl)acetyl]alanine 3-methylbut-2-enyl ester
N-[(3-chlorophenyl)acetyl]alanine cyclopropylmethyl ester
N-[(3-chlorophenyl)acetyl]alanine 2-thienylmethyl ester
N-[(3-chlorophenyl)acetyl]alanine (1-methylcyclopropyl) methyl ester
N-[(3-chlorophenyl)acetyl]alanine 3-thienylmethyl ester
N-[(3-chlorophenyl)acetyl]alanine 2-methylcyclopentyl ester
N-[(3-chlorophenyl)acetyl]alanine 2-methylprop-2-enyl ester
N-[(3-chlorophenyl)acetyl]alanine cyclohex-2-enyl ester
N-[(2-phenylbenzoxazol-5-yl)acetyl]alanine iso-butyl ester
N-[(3-methylthiophenyl)acetyl]alanine iso-butyl ester
N-4-[(2-furyl)acetyl]alanine iso-butyl ester
N-[(benzofuran-2-yl)acetyl]alanine iso-butyl ester
N-[(benzothiophen-3-yl)acetyl]alanine iso-butyl ester
N-[(2-chloro-5-thienyl)acetyl]alanine iso-butyl ester
N-[(3-methyl-isoxazol-5-yl)acetyl]alanine iso-butyl ester
N-[(2-phenylthiothienyl)acetyl]alanine iso-butyl ester
N-[(6-methoxybenzothiophen-2-yl)acetyl]alanine iso-butyl ester
N-[(3-phenyl-1,2,4-thiadiazol-5-yl)acetyl]alanine iso-butyl ester
N-[(2-phenyloxazol-4-yl)acetyl]alanine iso-butyl ester
N-[(3-methylphenyl)acetyl]alanine iso-butyl ester
N-[(2,5-difluorophenyl)acetyl]alanine iso-butyl ester
N-[(3,5-difluorophenyl)acetyl]alanine iso-butyl ester
N-[(3-thienyl)acetyl]alanine iso-butyl ester
N-[(4-methylphenyl)acetyl]alanine iso-butyl ester
N-(phenylacetyl)alanine (1-methoxycarbonyl)iso-butyl ester
N-[(3-nitrophenyl)acetyl]alanine iso-butyl ester
N-[(3,5-difluorophenyl)acetyl]alanine ethyl ester
N-[(3-nitrophenyl)acetyl]methionine ethyl ester
N-[(3-chlorophenyl)acetyl]alanine iso-butyl ester
N-[(3-chlorophenyl)acetyl]alanine 2-(N,N-dimethylamino) ethyl ester
2-[(3,5-dichlorophenyl)acetamido]hexanoic acid methyl ester
N-[(3,5-dichlorophenyl)acetyl]alanine iso-butyl ester
N-(cyclohexylacetyl)alanine iso-butyl ester
N-(cyclopentylacetyl)alanine iso-butyl ester
N-[(cyclohex-1-enyl)acetyl]alanine iso-butyl ester
N-[(3-chlorophenyl)acetyl]alanine 3-methylbut-2-enyl thioester
N-[(2-phenyl)-2-fluoroacetyl]alanine ethyl ester
N-(3,5-difluorophenylacetyl)phenylglycine methyl ester
N-(3,5-difluorophenylacetyl)phenylglycine iso-butyl ester
N-(cyclopentylacetyl)phenylglycine methyl ester
N-(cyclopentylacetyl)alanine methyl ester
N-(cyclopropylacetyl)phenylglycine methyl ester
N-(cyclopropylacetyl)alanine methyl ester
N-[(3-nitrophenyl)acetyl]methionine iso-butyl ester Still further, this invention provides for novel compounds of the formula III:

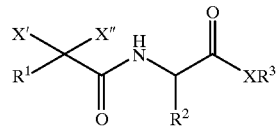

wherein $R^1$ is selected from the group consisting of
a) alkyl, alkenyl, alkcycloalkyl, phenyl-$(R)_m$-, naphthyl-$(R)_m$- wherein R is an alkylene group of from 1 to 8 carbon atoms and m is an integer equal to 0 or 1, cycloalkyl, cycloalkenyl, 3-pyridyl, 4-pyridyl and heteroaryl, other than 3- and 4-pyridyl, of 3 to 10 atoms and 1 to 4 heteroatoms selected from oxygen, sulfur and nitrogen wherein the heteroaryl group is optionally substituted with 1 to 3 substituents selected from the group consisting of alkyl, alkoxy, aryl, aryloxy, halo, nitro, thioalkoxy, and thioaryloxy with the proviso that for such heteroaryls when there is at least one nitrogen heteroatom, there is also at least one oxygen and/or sulfur heteroatom;

(b) a substituted phenyl group of formula II:

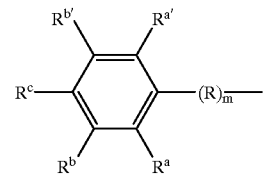

wherein R is alkylene of from 1 to 8 carbon atoms,
m is an integer equal to 0 or 1,
$R^a$ and $R^{a'}$ are independently selected from the group consisting of hydrogen, hydroxy, fluoro and methyl;
$R^b$ and $R^{b'}$ are independently selected from the group consisting of hydrogen, alkyl, alkoxy, aryl, cyano, cycloalkyl, halo, heteroaryl, heterocyclic, nitro, trihalomethyl, thioalkoxy, thioaryloxy, thioheteroaryloxy, and —C(O)$R^4$ where $R^4$ is selected from the group consisting of alkyl, aryl, alkoxy and aryloxy; and
$R^c$ is selected from the group consisting of hydrogen, alkyl, aryl, cyano, halo, nitro, and where $R^b$ and $R^c$ are fused to form a methylenedioxy ring with the phenyl ring; and
when $R^b$ and/or $R^{b'}$ and/or $R^c$ is fluoro, chloro, bromo and/or nitro, then $R^a$ and/or $R^{a'}$ can also be chloro; and
(c) 1- or 2-naphthyl-$(R)_m$- wherein R is an alkylene group of from 1 to 8 carbon atoms and m is an integer equal to 0 or 1 substituted at the 5, 6, 7 and/or 8 positions with 1 to 4 substituents selected from the group consisting alkyl, alkoxy, halo, cyano, nitro, trihalomethyl, and thioalkoxy;
$R^2$ is selected from the group consisting of hydrogen, alkyl, phenyl, alkylalkoxy, alkylthioalkoxy; and
$R^3$ is selected from the group consisting of —$(CH_2)_n$ $CR^{10}R^5R^6$ wherein n is an integer equal to 0, 1 or 2, $R^5$ and $R^6$ are independently selected from hydrogen, alkyl, alkenyl, aryl, heteroaryl, heterocyclic, —$NR^7R^8$ where $R^7$ and $R^8$ are independently hydrogen or alkyl, and —COO$R^9$ where $R^9$ is alkyl, and further wherein $R^5$ and $R^6$ can be joined to form a cycloalkyl group, a cycloalkenyl group, an aryl group, a heteroaryl group, and a heterocyclic group, and when $R^5$ and $R^6$ do not join to form an aryl or heteroaryl group, then $R^{10}$ is selected from hydrogen and alkyl with the proviso that when n is zero, then $R^{10}$ is hydrogen and and when n is greater than zero and $R^5$ and $R^6$ are joined to form an aryl or heteroaryl group, then $R^{10}$ becomes a bond within that group;

X is oxygen or sulfur;

X' is hydrogen, hydroxy or fluoro;

X" is hydrogen, hydroxy or fluoro, or X' and X" together form an oxo group, and pharmaceutically acceptable salts thereof with the provisos that:

when $R^1$ is phenyl, $R^2$ is —CH(CH$_3$)CH$_2$CH$_3$, X is oxygen, and X' and X" are hydrogen, then $R^3$ is not —CH$_2$CH$_3$ or —CH$_2$CH(CH$_3$)$_2$ when $R^1$ is phenyl, $R^3$ is —CH$_2$CH(CH$_3$)$_2$, X is oxygen, and X' and X" are hydrogen, then $R^2$ is not —CH(CH$_3$)$_2$ when $R^1$ is pyrid-3-yl, $R^2$ is ethyl, X is oxygen, and X' and X" are hydrogen, then $R^3$ is not —CH$_2$CH(CH$_3$)$_2$, when $R^1$ is indoxazin-3-yl, 2,4-dimethylthiazol-5-yl, 4-methyl-1,2,5-thiooxadizol-3-yl or 3,5-di(trifluoromethyl) phenyl, $R^2$ is methyl, X is oxygen, and X' and X" are hydrogen, then $R^3$ is not —CH$_2$CH(CH$_3$)$_2$, and when $R^1$ is —CH$^2$-phenyl, $R^3$ is —CH$_2$CH$_3$, X is oxygen, and X' and X" are hydrogen, then $R^2$ is not —CH$_2$CH(CH$_3$)$_2$;

and still with further proviso excluding the following known compound: N-(phenylacetyl)methionine ethyl ester.

Preferred compounds of formula m above include those set forth in Formula IV below:

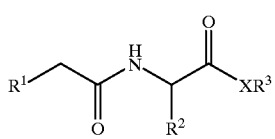

IV

| $R^1$ | $R^2$ | $R^3$ | X |
|---|---|---|---|
| —φ | —CH$_3$ | —CH$_2$CH(CH$_3$)$_2$ | O |
| —CH$_2$-φ | —CH$_3$ | —CH$_2$CH(CH$_3$)$_2$ | O |
| —CH(CH$_3$)CH$_2$CH$_3$ | —CH$_3$ | —CH$_2$CH(CH$_3$)$_2$ | O |
| 4-Cl-φ- | —CH$_3$ | —CH$_2$CH(CH$_3$)$_2$ | O |
| 3,4-Cl-φ- | —CH$_3$ | —CH$_2$CH(CH$_3$)$_2$ | O |
| pyrid-3-yl | —CH$_3$ | —CH$_2$CH(CH$_3$)$_2$ | O |
| 1-naphthyl | —CH$_3$ | —CH$_2$CH(CH$_3$)$_2$ | O |
| 2-naphthyl | —CH$_3$ | —CH$_2$CH(CH$_3$)$_2$ | O |
| —(CH$_2$)$_2$-φ | —CH$_3$ | —CH$_2$CH(CH$_3$)$_2$ | O |
| —(CH$_2$)$_3$-φ | —CH$_3$ | —CH$_2$CH(CH$_3$)$_2$ | O |
| pyrid-4-yl | —CH$_3$ | —CH$_2$CH(CH$_3$)$_2$ | O |
| 3,4-di-Cl-φ- | —CH$_2$CH$_3$ | —CH$_2$CH(CH$_3$)$_2$ | O |
| 3-CH$_3$O-φ- | —CH$_2$CH$_3$ | —CH$_2$CH(CH$_3$)$_2$ | O |
| 4-NO$_2$-φ- | —CH$_2$CH$_3$ | —CH$_2$CH(CH$_3$)$_2$ | O |
| 3,4-methylene-dioxyphenyl- | —CH$_2$CH$_3$ | —CH$_2$CH(CH$_3$)$_2$ | O |
| thien-3-yl | —CH$_2$CH$_3$ | —CH$_2$CH(CH$_3$)$_2$ | O |
| 4-Cl-φ- | —CH$_2$CH$_3$ | —CH$_2$CH(CH$_3$)$_2$ | O |
| 3-NO$_2$-φ- | —CH$_2$CH$_3$ | —CH$_2$CH(CH$_3$)$_2$ | O |
| 2-HO-φ- | —CH$_2$CH$_3$ | —CH$_2$CH(CH$_3$)$_2$ | O |
| 2-naphthyl | —CH$_2$CH$_3$ | —CH$_2$CH(CH$_3$)$_2$ | O |
| 2,4-di-Cl-φ- | —CH$_2$CH$_3$ | —CH$_2$CH(CH$_3$)$_2$ | O |
| 4-Br-φ- | —CH$_2$CH$_3$ | —CH$_2$CH(CH$_3$)$_2$ | O |
| 3-Cl-φ- | —CH$_2$CH$_3$ | —CH$_2$CH(CH$_3$)$_2$ | O |
| 3-F-φ- | —CH$_2$CH$_3$ | —CH$_2$CH(CH$_3$)$_2$ | O |
| benzothiazol-4-yl | —CH$_2$CH$_3$ | —CH$_2$CH(CH$_3$)$_2$ | O |
| 2-CH$_3$-φ- | —CH$_2$CH$_3$ | —CH$_2$CH(CH$_3$)$_2$ | O |
| 2-F-φ- | —CH$_2$CH$_3$ | —CH$_2$CH(CH$_3$)$_2$ | O |
| 4-F-φ- | —CH$_2$CH$_3$ | —CH$_2$CH(CH$_3$)$_2$ | O |
| 3-Br-φ- | —CH$_2$CH$_3$ | —CH$_2$CH(CH$_3$)$_2$ | O |
| 3-CF$_3$-φ- | —CH$_2$CH$_3$ | —CH$_2$CH(CH$_3$)$_2$ | O |
| thien-2-yl | —CH$_2$CH$_3$ | —CH$_2$CH(CH$_3$)$_2$ | O |
| φ- | —CH$_2$CH$_3$ | —CH$_2$CH(CH$_3$)$_2$ | O |
| φ- | —CH(CH$_3$)$_2$ | —CH$_2$CH(CH$_3$)CH$_2$CH$_3$ | O |
| φ- | —CH$_2$CH$_2$SCH$_3$ | —CH$_2$CH(CH$_3$)$_2$ | O |
| φ- | —CH$_2$CH(CH$_3$)$_2$ | —CH$_2$CH(CH$_3$)$_2$ | O |
| 3-Cl-φ- | —CH$_3$ | —CH$_2$CH=C(CH$_3$)$_2$ | O |
| 3-Cl-φ- | —CH$_3$ | —CH$_2$-cyclopropyl | O |

-continued

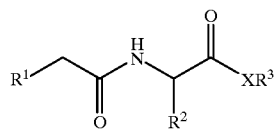

IV

| $R^1$ | $R^2$ | $R^3$ | X |
|---|---|---|---|
| 3-Cl-φ- | —CH$_3$ | —CH$_2$-2-thienyl | O |
| 3-Cl-φ- | —CH$_3$ | —CH$_2$C(CH$_2$)(CH$_2$)CH$_3$ (cyclopropyl methyl w/ CH$_3$) | O |
| 3-Cl-φ- | —CH$_3$ | —CH$_2$-3-thienyl | O |
| 3-Cl-φ- | —CH$_3$ | -(2-CH$_3$-cyclopentyl) | O |
| 3-Cl-φ- | —CH$_3$ | —CH$_2$C(CH$_3$)=CH$_2$ | O |
| 3-Cl-φ- | —CH$_3$ | -cyclohex-2-enyl | O |
| 2-phenyl-benzoxazol-5-yl | —CH$_3$ | —CH$_2$CH(CH$_3$)$_2$ | O |
| 3-CH$_3$S-φ- | —CH$_3$ | —CH$_2$CH(CH$_3$)$_2$ | O |
| furan-2-yl | —CH$_3$ | —CH$_2$CH(CH$_3$)$_2$ | O |
| benzofuran-2-yl | —CH$_3$ | —CH$_2$CH(CH$_3$)$_2$ | O |
| benzothien-3-yl | —CH$_3$ | —CH$_2$CH(CH$_3$)$_2$ | O |
| 2-chloro-thien-5-yl | —CH$_3$ | —CH$_2$CH(CH$_3$)$_2$ | O |
| 3-methyl-isoxazol-5-yl | —CH$_3$ | —CH$_2$CH(CH$_3$)$_2$ | O |
| 2-φ-S-thien-5-yl | —CH$_3$ | —CH$_2$CH(CH$_3$)$_2$ | O |
| 6-CH$_3$O-benzothiophen-2-yl | —CH$_3$ | —CH$_2$CH(CH$_3$)$_2$ | O |
| 3-phenyl-1,2,4-thiadiazol-5-yl | —CH$_3$ | —CH$_2$CH(CH$_3$)$_2$ | O |
| 2-φ-oxazol-4-yl | —CH$_3$ | —CH$_2$CH(CH$_3$)$_2$ | O |
| 3-CH$_3$-φ- | —CH$_3$ | —CH$_2$CH(CH$_3$)$_2$ | O |
| 2,5-di-F-φ- | —CH$_3$ | —CH$_2$CH(CH$_3$)$_2$ | O |
| 3,5-di-F-φ- | —CH$_3$ | —CH$_2$CH(CH$_3$)$_2$ | O |
| thien-3-yl | —CH$_3$ | —CH$_2$CH(CH$_3$)$_2$ | O |
| 4-CH$_3$-φ- | —CH$_3$ | —CH$_2$CH(CH$_3$)$_2$ | O |
| φ- | —CH$_3$ | —CH(CH(CH$_3$)$_2$)COOCH$_3$ | O |
| 3-NO$_2$-φ- | —CH$_3$ | —CH$_2$CH(CH$_3$)$_2$ | O |
| 3,5-di-F-φ | —CH$_3$ | —CH$_2$CH$_3$ | O |
| 3-NO$_2$-φ- | —CH$_2$CH$_2$SCH$_3$ | —CH$_2$CH$_3$ | O |
| 3-Cl-φ- | —CH$_3$ | —CH$_2$CH(CH$_3$)$_2$ | O |
| 3-Cl-φ- | —CH$_3$ | —CH$_2$CH$_2$N(CH$_3$)$_2$ | O |
| 3,5-di-Cl-φ- | —CH$_2$CH$_2$CH$_2$CH$_3$ | —CH$_3$ | O |
| 3,5-di-Cl-φ- | —CH$_3$ | —CH$_2$CH(CH$_3$)$_2$ | O |
| cyclohexyl | —CH$_3$ | —CH$_2$CH(CH$_3$)$_2$ | O |
| cyclopentyl | —CH$_3$ | —CH$_2$CH(CH$_3$)$_2$ | O |
| cyclohex-1-enyl | —CH$_3$ | —CH$_2$CH(CH$_3$)$_2$ | O |
| 3-Cl-φ- | —CH$_3$ | —CH$_2$CH=C(CH$_3$)$_2$ | S |
| 3,5-di-F-φ- | -φ | —CH$_3$ | O |
| 3,5-diF-φ | -φ | —CH$_2$CH(CH$_3$)$_2$ | O |
| cyclopentyl | -φ | —CH$_3$ | O |
| cyclopentyl | —CH$_3$ | —CH$_3$ | O |
| cyclopropyl | -φ | —CH$_3$ | O |
| cyclopropyl | —CH$_3$ | —CH$_3$ | O |
| 3-NO$_2$-φ | —CH$_2$CH$_2$SCH$_3$ | —CH$_2$CH(CH$_3$)$_2$ | O |

Another preferred compound of formula I above includes the compound wherein $R^1$ is phenyl, $R^2$ is fluoro and $R^3$ is methyl.

DETAILED DESCRIPTION OF THE INVENTION

As above, this invention relates to compounds which inhibit β-amyloid peptide release and/or its synthesis, and, accordingly, have utility in treating Alzheimer's disease. However, prior to describing this invention in further detail, the following terms will first be defined.

Definitions

The term "β-amyloid peptide" refers to a 3943 amino acid peptide having a molecular weight of about 4.2 kD, which peptide is substantially homologous to the form of the protein described by Glenner, et al.[1] including mutations and post-translational modifications of the normal β-amyloid peptide. In whatever form, the β-amyloid peptide is approximately a 3943 amino acid fragment of a large membrane-spanning glycoprotein, referred to as the β-amyloid precursor protein (APP). Its 43-amino acid sequence is:

```
 1
Asp Ala Glu Phe Arg His Asp Ser Gly Tyr

11
Glu Val His His Gln Lys Leu Val Phe Phe

21
Ala Glu Asp Val Gly Ser Asn Lys Gly Ala

31
Ile Ile Gly Leu Met Val Gly Gly Val Val

41
Ile Ala Thr (SEQ ID NO: 1)
``` or a sequence which is substantially homologous thereto.

"Alkyl" refers to monovalent alkyl groups preferably having from 1 to 10 carbon atoms and more preferably 1 to 6 carbon atoms. This term is exemplified by groups such as methyl, ethyl, n-propyl, isopropyl, n-butyl, iso-butyl, tert-butyl, n-hexyl, and the like.

"Alkylene" refers to divalent alkylene groups preferably having from 1 to 8 carbon atoms and more preferably 1 to 6 carbon atoms. This term is exemplified by groups such as methylene ($-CH_2-$), ethylene ($-CH_2CH_2-$), the propylene isomers (e.g., $-CH_2CH_2CH_2-$ and $-CH(CH_3)CH_2-$) and the like.

"Alkoxy" refers to the group "alkyl—O—" wherein alkyl is as defined herein. Preferred alkoxy groups include, by way of example, methoxy, ethoxy, n-propoxy, iso-propoxy, n-butoxy, tert-butoxy, sec-butoxy, n-pentoxy, n-hexoxy, 1,2-methylbutoxy, and the like.

"Alkylalkoxy" refers to the group "-alkylene—O—alkyl" wherein alkylene and alkyl are as defined herein. Such groups include, by way of example, methylenemethoxy ($-CH_2OCH_3$), ethylenemethoxy ($-CH_2CH_2OCH_3$), n-propylene-iso-propoxy ($-CH_2CH_2CH_2OCH(CH_3)_2$), methylene-tert-butoxy ($-CH_2-O-C(CH_3)_3$) and the like.

"Alkylthioalkoxy" refers to the group "-alkylene—S—alkyl" wherein alkylene and alkyl are as defined herein. Such groups include, by way of example, methylenethiomethoxy ($-CH_2SCH_3$), ethylenethiomethoxy ($-CH_2CH_2SCH_3$), n-propylene-iso-thiopropoxy ($-CH_2CH_2CH_2SCH(CH_3)_2$), methylene-tert-thiobutoxy ($-CH_2SC(CH_3)_3$) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl ($-CH=CH_2$), n-propenyl ($-CH_2CH=CH_2$), iso-propenyl ($-C(CH_3)=CH_2$), and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl ($-C\equiv CH$), propargyl ($-CH_2C\equiv CH$) and the like.

"Acyl" refers to the groups alkyl—C(O)—, aryl—C(O)—, and heteroaryl—C(O)— where alkyl, aryl and heteroaryl are as defined herein.

"Acylamino" refers to the group —C(O)NRR where each R is independently hydrogen or alkyl.

"Alkcycloalkyl" refers to the group -alkylene-cycloalkyl wherein alkylene and cycloalkyl are as defined herein.

"Aminoacyl" refers to the group —NRC(O)R where each R is independently hydrogen or alkyl.

"Acyloxy" refers to the groups alkyl—C(O)O—, aryl—C(O)O—, heteroaryl—C(O)O—, and heterocyclic—C(O)O— where alkyl, aryl, heteroaryl and heterocyclic are as defined herein.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, alkoxy, alkenyl, alkynyl, amino, aminoacyl, aryl, aryloxy, carboxyl, carboxylalkyl, acylamino, cyano, halo, nitro, heteroaryl, trihalomethyl, thioalkoxy, and the like. Preferred substituents include alkyl, alkoxy, halo, cyano, nitro, trihalomethyl, and thioalkoxy.

"Aryloxy" refers to the group aryl—O— wherein the aryl group is as defined above including optionally substituted aryl groups as also defined above. "Carboxylalkyl" refers to the group —C(O)O—alkyl where alkyl is as defined herein.

"Cycloalkyl" refers to cyclic alkyl groups of from 3 to 10 carbon atoms having a single cyclic ring or multiple condensed rings which can be optionally substituted with from 1 to 3 alkyl groups. Such cycloallyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 8 carbon atoms having a single cyclic ring and at least one point of internal unsaturation which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Halo" or "halogen" refers to fluoro, chloro, bromo and iodo and preferably is either fluoro or chloro.

"Heteroaryl" refers to a monovalent aromatic group of from 2 to 8 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of alkyl, alkoxy, aryl, aryloxy, halo, nitro, heteroaryl, thioalkoxy, thioaryloxy. Such heteroaryl groups can have a single ring (e.g., pyridyl or furyl) or multiple condensed rings (e.g., indolizinyl or benzothienyl). Preferred heteroaryls include pyridyl and furyl.

"Heterocycle" or "heterocyclic" refers to a monovalent (i.e. one point of attachment) saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of alkyl, alkoxy, aryl, aryloxy, halo, nitro, heteroaryl, thioalkoxy, thioaryloxy and the like. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

Examples of heterocycles and heteroaryls include, but are not limited to, furan, thiophene, thiazole, oxazole, benzothiazole, benzofuran, benzothiophene, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Thiol" refers to the group —SH.

"Thioalkoxy" refers to the groups —S—alkyl where alkyl is as defined herein.

"Thioaryloxy" refers to the group aryl—S— wherein the aryl group is as defined above including optionally substituted aryl groups as also defined above.

"Thioheteroaryloxy" refers to the group heteroaryl—S— wherein the heteroaryl group is as defined above including optionally substituted aryl groups as also defined above.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of formula I above are readily prepared via several divergent synthetic routes with the particular route selected relative to the ease of compound preparation, the commercial availability of starting materials, and the like.

A first synthetic method involves conventional coupling of an acetic acid derivative with a primary amine of an esterified amino acid as shown in reaction (1):

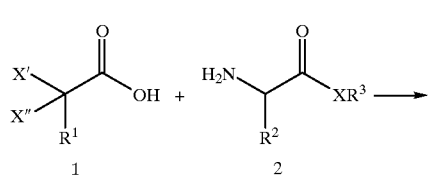

(1)

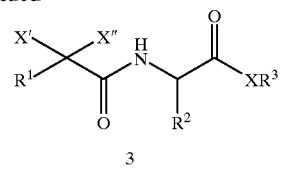

3 wherein $R^1$, $R^2$, $R^3$, X, X' and X" are as defined above.

Reaction (1) merely involves coupling of a suitable acetic acid derivative 1 with the primary amine of amino acid ester 2 under conditions which provide for the N-acetyl derivative 3. This reaction is conventionally conducted for peptide synthesis and synthetic methods used therein can also be employed to prepare the N-acetyl amino acid esters 3 of this invention. For example, well known coupling reagents such as carbodiimides or BOP (benzotriazol-1-yloxy-tris (dimethylamino)phosphonium hexafluorophosphate) with or without the use of well known additives such as N-hydroxysuccinimide, 1-hydroxybenzotriazole, etc. can be used to facilitate coupling. The reaction is conventionally conducted in an inert aprotic diluent such as dimethylformamide, dichloromethane, chloroform, acetonitrile, tetrahydrofuran and the like. Alternatively, the acid halide of compound I can be employed in reaction (1) and, when so employed, it is typically employed in the presence of a suitable base to scavenge the acid generated during the reaction. Suitable bases include, by way of example, triethylamine, diisopropylethylamine, N-methylmorpholine and the like.

Reaction (1) is preferably conducted at from about 0° C. to about 60° C. until reaction completion which typically occurs within I to about 24 hours. Upon reaction completion, N-acetyl amino acid ester 3 is recovered by conventional methods including precipitation, chromatography, filtration and the like.

In reaction (1), each of the reagents (acetic acid derivative 1 and amino acid ester 2) are well known in the art with a plurality of each being commercially available.

Alternatively, the synthesis described above in reaction (1) can be conducted on the amino acid ($XR^3$=OH) and subsequent to N-acetyl formation as described above, the carboxylic acid is then esterified with either the alcohol ($HOR^3$) or the thioalcohol ($HSR^3$) under conventional conditions to provide for the N-acetyl amino acid ester 3 which is a compound of formula I. For example, esterification procedures for $R^3$ groups containing an ester group can be achieved by using the methods of Losse, et al.[10]

In still a further embodiment, conventional transesterification techniques can be used to prepare a variety of different ester groups on the N-acetyl amino acid esters 3. Numerous techniques are known in the art to effect transesterification and each technique merely replaces the —$OR^3$ group on the ester of the N-acetyl amino acid ester 3 with a different —$OR^3$/—$SR^3$ group derived from the corresponding alcohol (i.e., $HOR^3$) or thioalcohol (i.e., $HSR^3$) and, in some cases, a catalyst such as titanium (IV) iso-propoxide is used to facilitate reaction completion. In one technique, the alcohol $HOR^3$ or thioalcohol $HSR^3$ is first treated with sodium hydride in a suitable diluent such as toluene to form the corresponding sodium alkoxide or thioalkoxide which is then employed to effect transesterification with the N-acetyl amino acid ester 3. The efficiency of this technique makes it particularly useful with high boiling and/or expensive alcohols.

In another transesterification technique, the N-acetyl amino acid ester 3 to be transesterified is placed in a large excess of the alcohol or thioalcohol which effects transesterification. A catalytic amount of sodium hydride is then added and the reaction proceeds quickly under conventional conditions to provide the desired transesterified product. Because this protocol requires the use of a large excess of alcohol or thioalcohol, this procedure is particularly useful when the alcohol is inexpensive.

Transesterification provides a facile means to provide for a multiplicity of $R^3$ substituents on the compounds of formula I above. In all cases, the alcohols and thioalcohols employed to effect transesterification are well known in the art with a significant number being commercially available.

Other methods for preparing the esters of this invention include, by way of example, first hydrolyzing the ester to the free acid followed by O-alkylation with a halo-$R^3$ group in the presence of a base such as potassium carbonate.

The compounds described herein can also be prepared by use of polymer supported forms of carbodiimide peptide coupling reagents. A polymer supported form of EDC, for example, has been described (*Tetrahedron Letters*, 34(48), 7685 (1993))[15]. Additionally, a new carbodiimide coupling reagent, PEPC, and its corresponding polymer supported forms have been discovered and are very useful for the preparation of the compounds of the present invention.

Polymers suitable for use in making a polymer supported coupling reagent are either commercially available or may be prepared by methods well known to the artisan skilled in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer's backbone must be inert to both the carbodiimide and reaction conditions under which the ultimate polymer bound coupling reagents will be used.

Certain hydroxymethylated resins may be converted into chloromethylated resins useful for the preparation of polymer supported coupling reagents. Examples of these hydroxylated resins include the 4-hydroxymethyl-phenylacetamidomethyl resin (Pam Resin) and 4-benzyloxybenzyl alcohol resin (Wang Resin) available from Advanced Chemtech of Louisville, Ky., USA (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis., USA (see Aldrich 1994–1995 catalog, page 899). Methods for the preparation of PEPC and its polymer supported forms are outlined in the following scheme.

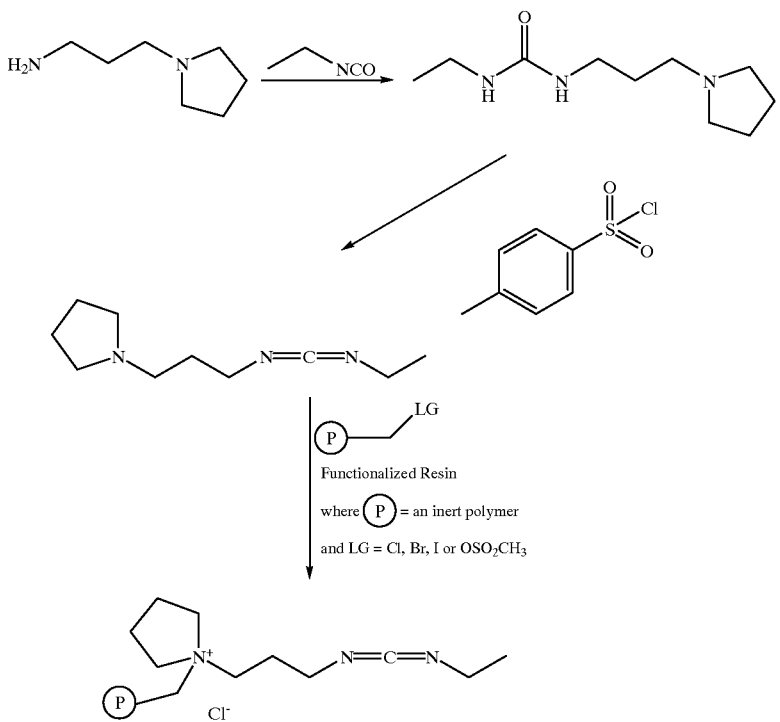

Such methods are described more fully in U.S. Provisional Patent Application 60/019,790, filed Jun. 14, 1996, the disclosure of which is incorporated herein by reference in its entirety. Briefly, PEPC is prepared by first reacting ethyl isocyanate with 1-(3-aminopropyl)pyrrolidine. The resulting urea is treated with 4-toluenesulfonyl chloride to provide PEPC. The polymer supported form is prepared by reaction of PEPC with an appropriate resin under standard conditions to give the desired reagent.

The carboxylic acid coupling reactions employing these reagents are performed at about ambient temperature to about 45° C., for from about 3 to 120 hours. Typically, the product may be isolated by washing the reaction with $CHCl_3$ and concentrating the remaining organics under reduced pressure. As discussed supra, isolation of products from reactions where a polymer bound reagent has been used is greatly simplified, requiring only filtration of the reaction mixture and then concentration of the filtrate under reduced pressure.

Still other methods for the preparation of esters are provided in the examples below.

In these synthetic methods, the starting materials can contain a chiral center (e.g., alanine) and, when a racemic starting material is employed, the resulting product is a mixture of R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of R,S enantiomers. Preferably, however, when a chiral product is desired, the chiral product corresponds to the L-amino acid derivative. Alternatively, chiral products can be obtained via purification techniques which separate enantiomers from a R,S mixture to provide for one or the other stereoisomer. Such techniques are well known in the art.

Pharmaceutical Formulations

When employed as pharmaceuticals, the compounds of formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |

-continued

| Ingredient | Quantity (mg/tablet) |
|---|---|
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
| --- | --- |
| Active Ingredient | 5.0 mg |
| Corn Oil | 1.0 mL |

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences,* Mace Publishing Company, Philadelphia, Pa., 17th ed. (1985).

Utility

The compounds and pharmaceutical compositions of the invention are useful in inhibiting β-amyloid peptide release and/or its synthesis, and, accordingly, have utility in treating Alzheimer's disease in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from AD in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of AD in the patient, the age, weight and general condition of the patient, and the like. Preferably, for use as therapeutics, the compounds described herein are administered at dosages ranging from about 0.1 to about 500 mg/kg/day.

In prophylactic applications, compositions are administered to a patient at risk of developing AD (determined for example by genetic screening or familial trait) in an amount sufficient to inhibit the onset of symptoms of the disease. An amount adequate to accomplish this is defined as "prophylactically effective dose." Amounts effective for this use will depend on the judgment of the attending clinician depending upon factors such as the age, weight and general condition of the patient, and the like. Preferably, for use as prophylactics, the compounds described herein are administered at dosages ranging from about 0.1 to about 500 mg/kg/day.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The following synthetic and biological examples are offered to illustrate this invention and are not to be construed in any way as limiting the scope of this invention.

EXAMPLES

In the discussion above and in the examples below, the following abbreviations have the following meanings. If an abbreviation is not defined, it has its generally accepted meaning.

bm=broad multiplet
BOC=tert-butoxycarbonyl
BOP=benzotriazol-1-yloxy-tis(dimethylamino) phosphonium hexafluorophosphate
bd=broad doublet
bs=broad singlet
CDI=1,1"-carbodiimidazole
d=doublet
dd=doublet of doublets
dq=doublet of quartets
dt=doublet of triplets
DMF=dimethylformamide
DMAP=dimethylaminopyridine
DMSO=dimethyl sulfoxide
EDC=1-(3-dimethyaminopropyl)-ethylcarbodiimide hydrochloride
eq.=equivalents
EtOAc=ethyl acetate
g=grams
h=hours
Hunig's base=diisopropylethylamine
kg=kilogram
L=liter
m=multiplet
M=molar
M %=mole percent
max=maximum
meq=milliequivalent
mg=milligram
mL=milliliter
mm=millimeter
mmol=millimole
N=normal
ng=nanogram
nm=nanometers
OD=optical density
P-EPC=1-(3-(1-pyrrolidinyl)propyl)-3ethylcarbodiimide
psi=pounds per square inch
φ=phenyl
q=quartet
quint.=quintet
rpm=rotations per minute
s=singlet
t=triplet
TFA=trifluoroacetic acid
THF=tetrahydrofuran
tlc=thin layer chromatography
μL=microliter
UV=ultraviolet Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates that the compound or reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa., USA; the term "Bachem" indicates that the compound or reagent is commercially available from Bachem Bioscience Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; and the term "TCI" indicates that the compound or reagent is commercially available from TCI America, 9211 North Harborgate St., Portland, Oreg., 97203, OR, USA; the term "Alfa" indicates that the compound or reagent is commercially available from Johnson Matthey Catalog Company, Inc. 30 Bond Street, Ward Hill, Md. 01835–0747; and the term "Nova Biochem" indicates that the compound or reagent is commercially available from NovaBiochem USA, 10933 North Torrey Pines Road, P.O. Box 12087, La Jolla Calif. 92039–2087.

In the examples below, all temperatures are in degrees Celsius (unless otherwise indicated) and the following general procedures were used to prepare the compounds as indicated.

GENERAL PROCEDURE A

Coupling of $R^1PC(X')(X'')C(O)Cl$ with $H^2NCH(R^2)C(O)XR^3$

To a stirred solution of (D,L)-alanine iso-butyl ester hydrochloride (from Example B below) (4.6 mmol) in 5 mL of pyridine was added 4.6 mmol of an acid chloride. Precipitation occurred immediately. The mixture was stirred for 3.5 h, diluted with 100 mL of diethyl ether, washed with 10% HCl three times, brine once, 20% potassium carbonate once and brine once. The solution was dried over magnesium sulfate, filtered, and evaporated at reduced pressure to yield the product. Other amino acid esters may also be employed in this procedure.

GENERAL PROCEDURE B

Coupling of $R^1C.(X')(X'')C(O)OH$ with $H^2NCH(R^2)C(O)XR^3$

A solution of the acid (3.3 mmol) and CDI in 20 mL THF was stirred for 2 h. L-alanine iso-butyl ester hydrochloride (from Example B below) (3.6 mmol) was added, followed by 1.5 mL (10.8 mmol) of triethylamine. The reaction mixture was stirred overnight. The reaction mixture was diluted with 100 mL of diethyl ether, washed with 10% HCl three times, brine once, 20% potassium carbonate once and brine once. The solution was dried over magnesium sulfate, filtered, and evaporated at reduced pressure to yield the product. Other amino acid esters may also be employed in this procedure.

GENERAL PROCEDURE C

Esterification of $R^1C(X')(X'')C(O)NHCH(R^2)C(O)OH$ With $HOR^3$

To a stirred solution of phenylacetylvaline (1.6470 g, 7.0 mmol) in 20 mL THF was added CDI (1.05 g, 6.5 mmol) and the mixture was stirred for 1.5 h. 2-Methylbutanol (0.53 g, 6 mmol) was added the mixture, followed by addition of NaH (0.16 g, 6.5 mmol). Bubbling occurred immediately. The reaction mixture was stirred overnight. The reaction mixture was diluted with 100 mL of diethyl ether, washed with 10% HCl three times, brine once, 20% potassium carbonate once and brine once. The solution was dried over magnesium sulfate, filtered, and evaporated at reduced pressure to yield the product. Other N-acyl amino acids and alcohols may also be employed in this procedure.

GENERAL PROCEDURE D

Ester Hydrolysis to the Free Acid

Ester hydrolysis to the free acid was conducted by conventional methods. Below are two examples of such conventional deesterification methods.

To the ester in a 1:1 mixture of $CH_3OH/H_2O$ was added 2–5 equivalents of $K_2CO_3$. The mixture was heated to about 50° C. for about 0.5 to 1.5 hours until tlc showed complete reaction. The reaction was cooled to room temperature and the methanol was removed at reduced pressure. The pH of the remaining aqueous solution was adjusted to about 2, and ethyl acetate was added to extract the product. The organic phase was then washed with saturated aqueous NaCl and dried over $MgSO_4$. The solution was stripped free of solvent at reduced pressure to yield the product.

The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was diluted with EtOAc, the layers were separated and the aqueous layer acidified to pH 2. The aqueous layer was back extracted with EtOAc, the combined organics were dried over $Na_2SO_4$ and the solvent was removed under reduced pressure after filtration. The residue was purified by conventional methods (e.g., recrystallization).

The following exemplifies this later example. The methyl ester of 3-$NO_2$ phenylacetyl alanine 9.27 g (0.0348 mols) was dissolved in 60 mL dioxane and 15 mL of $H_2O$ and adding LiOH (3.06 g, 0.0731 mol) that has been dissolved in 15 mL of $H_2O$. After stirring for 4 hours, the dioxane was removed under reduced pressure and the residue diluted with EtOAc, the layers were separated and the aqueous layer acidified to pH 2. The aqueous layer was back extracted with EtOAc (4×100 mL), the combined organics were dried over $Na_2SO_4$ and the solvent was removed under reduced pressure after filtration. The residue was recrystallized from EtOAc/isooctane giving 7.5 g (85%) of 3-nitrophenylacetyl alanine. $C_{11}H_{12}N_2O_5$ requires C=52.38, H=4.80, and N=11.11. Analysis found C=52.54, H=4.85, and N=11.08. $[\alpha]_{23}$=29.9 @ 589 nm.

GENERAL PROCEDURE E

Low Temperature BOP Coupling of Acid and Alcohol

A solution of methylene chloride containing the carboxylic acid (100M %) and N-methyl morpholine (150 M %) was cooled to −20° C. under nitrogen. BOP (105 M %) was added in one portion and the reaction mixture was maintained at −20° C. for 15 minutes. The corresponding alcohol (120 M %) was added and the reaction mixture was allowed to warm to room temperature and stirred for 12 hours. The reaction mixture was then poured into water and extracted with ethyl acetate (3×). The combined ethyl acetate portions were backwashed with saturated aqueous citric acid (2×), saturated aqueous sodium bicarbonate (2×), brine (1×), dried over anhydrous magnesium sulfate or sodium sulfate and the solvent removed under reduced pressure to yield the crude product.

GENERAL PROCEDURE F

EDC Coupling of Acid and Amine

The acid derivative was dissolved in methylene chloride. The amine (1 eq.), N-methylmorpholine (5 eq.), and hydroxybenzotriazole monohydrate (1.2 eq.) were added in sequence. The reaction was cooled to about 0° C. and then 1.2 eq. of 1-(3-dimethylaminopropyl)-3-ethylcarbodiimide hydrochloride was added. The solution was allowed to stir overnight and come to room temperature under N. pressure. The reaction mix was worked up by washing the solution with saturated, aqueous $Na_2CO_3$, 0.1M citric acid, and brine before drying with $NaSO_4$ and removal of solvents to yield crude product. Pure products were obtained by flash chromatography in an appropriate solvent.

GENERAL PROCEDURE G

EDC Coupling of Acid and Amine

A round bottom flask was charged with carboxylic acid (1.0 eq.), hydroxybenzotriazole hydrate (1.1 eq.) and amine (1.0 eq.) in THF under nitrogen atmosphere. An appropriate amount (1.1 eq. for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in EtOAc (or similar solvent)/water. The organic layer was washed with saturated aqueous sodium bicarbonate solution, 1N HCl, brine and dried over anhydrous sodium sulfate. In some cases, the isolated product was analytically pure at this stage while, in other cases, purification via chromatography and/or recrystallization was required prior to biological evaluation.

GENERAL PROCEDURE H

Coupling of $R^1C(X')(X'')C(O)Cl$ with $H_2NCH(R^2)C(O)XR^3$

An excess of oxalyl chloride in dichloromethane was added to the acid derivative together with one drop of DMF. The resulting mixture was stirred for about 2 hours or until bubbling ceases. The solvent was then removed under reduced pressure and rediluted with dry methylene chloride. To the resulting solution was added about 1.1 eq. of the appropriate amino acid ester and triethylamine (1.1 eq. in methylene chloride). The system was stirred at room temperature for 2 hours and then the solvent was removed under reduced pressure. The residue was dissolved in ethyl acetate, washed with 1N HCl followed by 1N NaOH. The organic layer was dried over anhydrous soldium sulfate, filtered and the solvent removed under reduced pressure to provide for the desired product.

GENERAL PROCEDURE I

P-EPC coupling

P-EPC coupling employs an amino acid ester and a substituted acetic acid compound. The acetic acid derivative is well known in the art and is typically commercially available. The amino acid ester is prepared by conventional methods from the known and typically commercially available N-BOC amino acid as described in GENERAL PROCEDURE J below.

Specifically, the appropriate amino ester free base (0.0346 mmols) and substituted phenylacetic acid (0.069 mmols) were dissolved in 2.0 mL $CHCl_3$ (ETOH free), treated with 150 mg of P-EPC (0.87 meq./g) and the reaction was mixed for 4 days at 23° C. The reaction was filtered through a plug of cotton, rinsed with 2.0 mL of $CHCl_3$ and the filtrate evaporated under a stream of nitrogen. The purity of each sample was determined by $^1$H NMR and ranged from 50% to >95%. Between 8.0 and 15.0 mg of final product was obtained from each reaction and was tested without additional purification.

GENERAL PROCEDURE J

Synthesis of Amino Acid Esters From the Corresponding N-BOC Amino Acid

A. Esterification of the Acid.

The N-BOC amino acid was dissolved in dioxane and treated with an excess of alcohol (~1.5 eq.) and catalytic DMAP (100 mg) at 0° C. Stirring was continued until reaction completion whereupon the product was recovered by conventional methods.

B. Removal of N-BOC Group.

The N-BOC protected amino acid was dissolved in methylene chloride (0.05M and treated with 10 eq. of TFA at room temperature under a nitrogen atmosphere. The reaction was monitored by tlc until starting material was consumed usually within 1–5 hours. An additional 10 eq. of TFA was added to the reaction if the starting material was still present after 5 hours. The reaction was carefully neutralized with $Na_2CO_3$, separated, the organic layer washed with brine and dried over anhydrous $Na_2SO_4$. The crude amine was then used without purification.

Specific exemplification of these procedures are as follows:

1. Racemic (+/−)-N-BOC-α-amino butyric acid (Aldrich) (9.29 g, 0.0457 mol) was dissolved in 100 mL of dioxane and treated with iso-butyl alcohol (6.26 mL, 0.0686 mol), EDC (8.72 g, 0.0457) and catalytic DMAP (100 mg) at 0° C. After stirring for 17 hours, the organics were evaporated at reduced pressure, the residue diluted with EtOAc washed with $NaHCO_3$, brine and dried over $Na_2SO_4$. Evaporation yields 8.42 g (71%) of an oil. $C_{13}H_{25}NO_4$ requires: C=60.21, H=9.72, and N=5.40. Anal found: C=59.91, H=9.89, and N=5.67.

The above N-BOC amino acid ester (8.00 g, 0.032 mol) was deprotected as above giving 3.12 g (61%) of the free base as a colorless oil which solidifies upon standing.

2. L-N-BOC-alanine (Aldrich) (8.97 g, 0.047 mol) was dissolved in 100 mL of $CH_2Cl_2$, iso-butyl alcohol (21.9 mL, 0.238 mol) and treated with DMAP (100 mg) and EDC (10.0 g, 0.52 mol) at 0° C. The mixture was stirred for 17 hours, diluted with $H_2O$, washed with 1.0 N HCl, $NaHCO_3$, then brine and the organics were dried over $Na_2SO_4$. Filtration and evaporation yields 11.8 g (quantitative) of L-N-BOC alanine iso-butyl ester which is contaminated with a small amount of solvent. A sample was vacuum dried for analytical analysis. $C_{12}H_{23}NO_4$ requires: C=58.79, H=9.38, and N=5.71. Anal found: C=58.73, H=9.55, and N=5.96.

The above N-BOC amino acid ester (11.8 g, 0.0481 mol) was deprotected as above. The free base was converted to the corresponding HCl salt using saturated HCl (g)/EtOAc to give L-N-alanine iso-butyl ester hydrochloride. Obtained 4.2 g (48%) of a colorless solid. $C_7H_{15}NO_2$. HCl requires: C=46.28, H=8.88, and N=7.71. Anal found: C=46.01, H=8.85, and N=7.68.

GENERAL PROCEDURE K

Methyl ester formation from amino acids

The amino acid (amino acid or amino acid hydrochloride) is suspended in methanol and chilled to 0° C. HCl gas is bubbled through this solution for 5 minutes. The reaction is allowed to warm to room temperature then stirred for 4 hours. The solvents are then removed at reduced pressure to afford the desired amino acid methyl ester hydrochloride. This product is usually used without further purification.

Example A

Synthesis of free and polymer bound PEPC

N-ethyl-N'-3-(1-pyrrolidinyl)propylurea

To a solution of 27.7 g (0.39 mol) ethyl isocyanate in 250 mL chloroform was added 50 g (0.39 mol) 3-(1-pyrrolidinyl) propylamine dropwise with cooling. Once the addition was complete, the cooling bath was removed and the reaction mixture stirred at room temperature for 4 hours. The reaction mixture was then concentrated under reduced pressure to give 74.5 g (96.4%) of the desired urea as a clear oil.

1-(3-(1-pyrrolidinyl)propyl)-3-ethylcarbodiimide (P-EPC)

To a solution of 31.0 g (0.156 mol) N-ethyl-N'-3-(1-pyrrolidinyl)propyl-urea in 500 mL dichloromethane was added 62.6 g (0.62 mol) triethylamine and the solution was cooled to 0° C. To this solution were then added 59.17 g (0.31 mol) 4-toluenesulfonyl chloride in 400 mL dichloromethane dropwise at such a rate as to maintain the reaction at 0–5° C. After the addition was complete, the reaction mixture was warmed to room temperature and then heated to reflux for 4 hours. After cooling to room temperature, the reaction mixture was washed with saturated aqueous potassium carbonate (3×150 mL). The aqueous phases were combined and extracted with dichloromethane. All organic phases were combined and concentrated under reduced pressure. The resultant orange slurry was suspended in 250 mL diethyl ether and the solution decanted off from the solid. The slurry/decantation process was repeated 3 more times. The ether solutions were combined and concentrated under reduced pressure to give 18.9 g (67%) of the desired product as a crude orange oil. A portion of the oil was distilled under vacuum to give a colorless oil distilling at 78–82° C. (0.4 mm Hg).

Preparation of a polymer supported form of 1-(3-(1-pyrrolidinyl)propyl)-3-ethylcarbodiimide (P-EPC)

A suspension of 8.75 g (48.3 mmol) 1-(3-(1-pyrrolidinyl)propyl)-3-ethylcarbodiimide and 24.17 g (24.17 mmol) Merrifield's resin (2% cross-linked, 200–400 mesh, chloromethylated styrene/divinylbenzene copolymer, 1 meq. Cl/g) in dimethylformamide was heated at 100° C. for 2 days. The reaction was cooled and filtered and the resulting resin washed sequentially with 1L DMF, 1L THF and 1L diethyl ether. The remaining resin was then dried under vacuum for 18 hours.

Example B

Preparation of alanine iso-butyl ester hydrochloride

A mixture of 35.64 g (0.4 mol) of (D,L)-alanine (Aldrich) (or L-alanine (Aldrich)); 44 mL (0.6 mol) of thionyl chloride (Aldrich) and 200 mL of isobutanol was refluxed for 1.5 hours and the volatiles were removed completely on a rotavapor of 90° C. under reduced pressure to give (D,L)-alanine iso-butyl ester hydrochloride (or L-alanine iso-butyl ester hydrochloride), which was pure enough to be used for further transformations.

Example C

Preparation of 3,5-dichlorophenylacetic acid

To a solution of 3.5 g of 3,5-dichlorobenzyl alcohol (Aldrich) in 75 mL of dichloromethane at 0° C. was added 1.8 mL of methane sulfonylchloride followed by 3.5 mL of triethylamine added dropwise. After 2 hours the solution was diluted to 150 mL with dichloromethane, washed with 3N HCl, saturated aqueous $NaHCO_3$ dried with $Na_2SO_4$ and the solvents removed to yield the desired 3,5-dichlorobenzyl methanesulfonate as a yellow oil that was used without purification.

The crude sulfonate was dissolved in 50 mL of DMF at 0° C. and then 3 g of KCN was added. After 2 hours an additional 50 mL of DMF was added and the solution was stirred for 16 hours. The red solution was diluted with 1 L of $H_2O$ and acidified to pH 3 with 3N HCl. The aqueous solution was extracted with dichloromethane. The combined organics were washed with 3N HCl, dried with $Na_2SO_4$ and the solvents removed at reduced pressure to yield crude 3,5-dichlorophenylacetonitrile which was used without purification.

The nitrile was added to a mixture of 40 mL of concentrated sulfuric acid and 50 mL $H_2O$ and heated to reflux for 48 hours, cooled to room temperature and stirred for 48 hours. The reaction was diluted into 1 L of crushed ice, warmed to room temperature and extracted with 2×200 mL of dichloromethane and 2×200 mL of ethylacetate. Both sets of organics were combined and washed with saturated aqueous $NaHCO_3$. The $NaHCO_3$ fractions were combined and acidified to pH 1 with 3N HCl. The white solid was too fine to filter and was extracted out with 2×200 mL of dichloromethane. The combined organics were dried with $Na_2SO_4$ and the solvents removed at reduced pressure to yield crude 3,5-dichlorophenylacetic acid as a white solid. The solid was slurried with hexane and filtered to get 1.75 g of white solid.

NMR ($CDCl_3$): (in ppm) 3.61 (s, 2H), 7.19 (s,1H), 7.30 (s, 1H)

Example D

Synthesis of N-(3-chlorophenylacetyl)alanine

The title compound was prepared using L-alanine (Nova Biochem) and 3-chlorophenyl acetic acid (Aldrich) by following General Procedures F or G, followed by hydrolysis using General Procedure D.

Example 1

Synthesis of N-(phenylacetyl)-D,L-alanine iso-butyl ester

Following General Procedure A above and using phenylacetyl chloride (Aldrich) and D,L-alanine iso-butyl ester hydrochloride (from Example B above), the title compound was prepared. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=7.23–7.36 (m, 5H), 6.18 (d, 1H), 4.58 (t, J=7.3 Hz, 1H), 3.87 (m, 2H), 3.57 (s, 2H), 1.90 (m, 1H), 1.34 (d, J=7.2 Hz, 3H), 0.89 (d, J=6.8 Hz, 6H).

$^{13}$C-nmr ($CDCl_3$): δ=172.7, 170.3, 134.5, 129.2, 128.8, 127.2, 71.3, 48.1, 43.4, 27.5, 18.8, 18.3.

$C_{15}H_{21}NO_3$ (MW=263.34; Mass Spectroscopy (MH$^+$=264))

Example 2

Synthesis of N-(3-phenylpropionyl)-D,L-alanine iso-butyl ester

Following General Procedure A above and using 3-phenylpropionyl chloride (Aldrich) and D,L-alanine iso-butyl ester hydrochloride (from Example B above), the title compound was prepared as a solid having a melting point of from 51°–54° C. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=7.25 (m, 2H), 7.19 (m, 3H), 6.28 (d, J=7.2 Hz, 1H), 4.58 (quint., J=7.2 Hz, 1H), 3.89 (m, 2H), 2.95 (t, J=7.7 Hz, 2H), 2.50 (m, 2H), 1.92 (m, 1H), 1.33 (d, J=7.1 Hz, 3H), 0.91 (d, J=6.7 Hz, 6H).

$^{13}$H-nmr ($CDCl_3$): δ=173.0, 171.5, 140.6, 128.3, 128.1, 126.0, 71.2, 47.8, 37.9, 31.4, 27.5, 18.79, 18.77, 18.3.

$C_{16}H_{23}NO_3$ (MW 277.37, Mass Spectroscopy (MH$^+$278))

Example 3

Synthesis of N-(3-methylpentanoyl)-L-alanine iso-butyl ester

Following General Procedure B and using 3-methylpentanoic acid (Aldrich) and L-alanine iso-butyl ester hydrochloride (from Example B above), the title compound was prepared as an oil. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=6.08 (d, J=5.9 Hz, 1H), 4.62 (quint., J=7.3 Hz, 1H), 3.92 (m, 2H), 2.22 (m, 1H), 1.84–2.00 (m, 3H), 1.40 (d, J=7.2 Hz, 3H), 1.35 (m, 1H), 1.20 (m, 1H), 0.85–0.96 (m, 12H).

$^{13}$C-nmr (CDCl$_3$): δ=173.3, 172.1, 71.4, 47.9, 43.9, 32.3, 29.38, 29.35, 27.6, 19.10, 19.06, 18.93, 18.91, 18.72, 18.67, 11.3.

C$_{13}$H$_{25}$NO$_3$ (MW=243.35, Mass Spectroscopy (MH$^+$ 244))

Example 4

Synthesis of N-[(4-chlorophenyl)acetyl]-L-alanine iso-butyl ester

Following General Procedure B and using 4-chlorophenylacetic acid (Aldrich) and L-alanine iso-butyl ester hydrochloride (from Example B above), the title compound was prepared as a solid having a melting point of 111°–113° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=7.30 (d, J=8.2 Hz, 2H), 7.21 (d, J=8.3 Hz, 2H), 6.18 (d, J=5.5 Hz, 1H), 4.57 (quint., J=7.2 Hz, 1H), 3.88 (m, 2H), 3.53 (s, 2H), 1.91 (m, 1H), 1.36 (d, J=7.1 Hz, 3H), 0.90 (d, J=6.8 Hz, 6H).

$^{13}$C-nmr (CDCl$_3$): δ=172.8, 169.8, 133.1, 133.0, 130.6, 128.9, 71.4, 48.2, 42.6, 27.6, 18.85, 18.82, 18.4.

C$_{15}$H$_{20}$NO$_3$Cl (MW=297.78, Mass Spectroscopy (MH$^+$ 298))

Example 5

Synthesis of N-[(3,4-dichlorophenyl)acetyl]-L-alanine iso-butyl ester

Following General Procedure B and using 3,4-dichlorophenylacetic acid (Aldrich) and L-alanine iso-butyl ester hydrochloride (from Example B above), the title compound was prepared as a solid having a melting point of 81°–83° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.90 (d, J=6.8 Hz, 6H), 1.38 (d, J=7.1 Hz, 3H), 1.91 (m, 1H), 3.50 (s, 2H), 3.90 (m, 2H), 4.57 (quint., J=7.1 Hz, 1H), 6.31 (d, J=4.9 Hz, 1H), 7.12 (m, 1H), 7.38 (m, 2H).

$^{13}$C-nmr (CDCl$_3$): δ=18.4, 18.8, 18.9, 27.6, 42.2, 48.3, 71.5, 128.6, 130.6, 131.2, 131.3, 132.6, 134.7, 169.2, 172.8.

C$_{15}$H19NO$_3$Cl$_2$ (MW=332.23, Mass Spectroscopy (MH$^+$ 332))

Example 6

Synthesis of N-[(4-methylphenyl)acetyl]-D,L-alanine iso-butyl ester

Following General Procedure B and using 4-methylphenylacetic acid (Aldrich) and D,L-alanine iso-butyl ester hydrochloride (from Example B above), the title compound was prepared as a solid having a melting point of 102°–104° C. The reaction was monitored by tlc on silica gel (Rf=0.6 in 33% ethyl acetate/hexanes) and purification was by extraction with Et$_2$O followed by washes with aqueous K$_2$CO$_3$ and aqueous HCl.

NMR data was as follows:

$^1$H-nmr (CDCl$_3$): δ=0.90 (d, J=6.7 Hz, 6H), 1.35 (d, J=7.2 Hz, 3H), 1.91 (m, 1H), 2.34 (s, 3H), 3.55 (s, 2H), 3.88 (m, 2H), 4.58 (m, 1H), 6.05 (bd, 1H), 7.16 (s, 4H).

$^{13}$C-nmr (CDCl$_3$): δ=18.5, 18.85, 18.87, 21.0, 27.6, 43.1, 48.1, 71.3, 129.2, 129.6, 131.3, 136.9, 170.6, 172.8.

C$_{16}$H$_{23}$NO$_3$ (MW=277.37, Mass Spectroscopy (MH$^+$ 278))

Example 7

Synthesis of N-[(3-pyridyl)acetyl]-D,L-alanine iso-butyl ester

Following General Procedure F and using 3-pyridylacetic acid hydrochloride (Aldrich) and D,L-alanine iso-butyl ester hydrochloride (from Example B above), the title compound was prepared as a solid having a melting point of 62°–64° C. The reaction was monitored by tlc on silica gel (Rf=0.48 10% methanol/dichloromethane) and purification was by silica gel chromatography.

NMR data was as follows:

$^1$H-nmr (CDCl$_3$): δ=8.40 (d, J=2.8, 2H); 7.6 (m, 1H): 7.16 (m, 2H); 4.5 (quint., J=7.2, 7.2, 1H); 3.8 (m, 2H); 3.48 (s, 2H); 1.8 (m, 1H); 1.30 (d, J=7.2, 3H); 0.81 (d, J=6.7, 6H).

$^{13}$C-nmr (CDCl$_3$): δ=173.4, 170.1, 150.6, 148.8, 137.4, 131.4, 124.1, 71.9, 48.9, 40.6, 28.1, 19.5, 19.4, 18.6.

C$_{14}$H$_{20}$N$_2$O$_3$ (MW=264, Mass Spectroscopy (MH$^+$265))

Example 8

Synthesis of N-[(1-naphthyl)acetyl]-L-alanine iso-butyl ester

Following General Procedure B and using 1-naphthylacetic acid (Aldrich) and L-alanine iso-butyl ester hydrochloride (from Example B above), the title compound was prepared as a solid having a melting point of 69°–73° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.83 (m, 6H), 1.25 (d, J=7.1 Hz, 3H), 1.81 (m, 1H), 3.79 (m, 2H), 4.04 (2s, 2H), 4.57 (quint., J=7.3 Hz, 1H), 5.99 (d, J=7.1 Hz, 1H), 7.44 (m, 2H), 7.53 (m, 2H), 7.85 (m, 2H), 7.98 (m, 1H).

$^{13}$C-nmr (CDCl$_3$): δ=18.2, 18.81, 18.83, 27.5, 41.5, 48.2, 71.3, 123.7, 125.6, 126.1, 126.6, 128.2, 128.5, 128.7, 130.7, 132.0, 133.9, 170.3, 172.5.

C$_{19}$H$_{23}$NO$_3$ (MW=313.40, Mass Spectroscopy (MH$^+$ 314))

Example 9

Synthesis of N-[(2-naphthyl)acetyl]-L-alanine iso-butyl ester

Following General Procedure B and using 2-naphthylacetic acid (Aldrich) and L-alanine iso-butyl ester hydrochloride (from Example B above), the title compound was prepared as a solid having a melting point of 128°–129° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.86 (m, 6H), 1.35 (d, J=7.1 Hz, 3H), 1.78 (m, 1H), 3.76 (s, 2H), 3.87 (m, 2H), 4.62 (quint., J=7.2 Hz, 1H), 6.13 (d, J=7.1 Hz, 1H), 7.41 (m, 1H), 7.48 (m, 2H), 7.74 (s, 1H), 7.83 (m, 3H).

$^{13}$C-nmr (CDCl$_3$): δ=18.4, 18.82, 18.85, 27.6, 43.7, 48.2, 71.4, 125.9, 126.3, 127.2, 127.6, 127.7, 128.2, 128.7, 132.0, 132.5, 133.5, 170.3, 172.8.

$C_{19}H_{23}NO_3$ (MW=313.40, Mass Spectroscopy (MH$^+$ 314)).

Example 10

Synthesis of N-(4-phenylbutanoyl)-L-alanine iso-butyl ester

Following General Procedure B and using 4-phenylbutanoic acid (Aldrich) and L-alanine iso-butyl ester hydrochloride (from Example B above), the title compound was prepared as an oil. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.92 (d, J=6.7 Hz, 6H), 1.38 (d, J=7.1 Hz, 3H), 1.96 (m, 3H), 2.21 (t, J=7.1 Hz, 2H), 2.64 (t, J=7.3 Hz, 2H), 3.90 (m, 2H), 4.59 (quint., J=7.2 Hz, 1H), 6.31 (d, 1H), 7.16 (m, 3H), 7.24 (m, 2H).

$^{13}$C-nmr (CDCl$_3$): δ=18.3, 18.75, 18.78, 26.8, 27.5, 34.9, 35.3, 47.8, 71.2, 125.7, 128.2, 128.3, 141.3, 172.1, 173.0.

$C_{17}H_{25}NO_3$ (MW=291.39, Mass Spectroscopy (MH$^+$ 292)).

Example 11

Synthesis of N-(5-phenylpentanoyl)-L-alanine iso-butyl ester

Following General Procedure B and using 5-phenylpentanoic acid (Aldrich) and L-alanine iso-butyl ester hydrochloride (from Example B above), the title compound was prepared as an oil. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=7.23 (m, 2H), 7.17 (m, 3H), 6.30 (d, 1H), 4.59 (quint., J=7.3 Hz, 1H), 3.91 (m, 2H), 2.61 (t, J=7.2 Hz, 2H), 2.22 (t, J=7.2 Hz, 2H), 1.93 (m, 1H), 1.66 (m, 4H), 1.38 (d, J=7.2 Hz, 3H), 0.92 (d, J=6.7 Hz, 6H).

$^{13}$C-nmr (CDCl$_3$): δ=173.1, 172.3, 142.0, 128.2, 128.1, 125.6, 71.2, 47.8, 36.1, 35.5, 30.8, 27.5, 25.0, 18.80, 18.77, 18.4.

$C_{18}H_{27}NO_3$ (MW=305.39, Mass Spectroscopy (MH$^+$ 306)).

Example 12

Synthesis of N-[(4-pyridyl)acetyl]-D,L-alanine iso-butyl ester

Following General Procedure F and using 4-pyridylacetic acid hydrochloride (Aldrich) and (D,L)-alanine iso-butyl ester hydrochloride (from Example B above), the title compound was prepared as a solid having a melting point of 64°–66° C. The reaction was monitored by tlc on silica gel (Rf=0.43 10% methanol/dichloromethane) and purification was by silica gel chromatography.

NMR data was as follows:

$^1$H-nmr (CDCl$_3$): δ=8.51 (dd, J=1.6, 2.8, 1.6, 2H); 7.23 (dd, J=4.3, 1.6, 4.4, 2H); 6.71 (d, J=6.8, 1H); 4.56 (quint., J=7.3, 7.2, 1H); 3.88 (m, 2H); 3.53 (s, 2H); 1.89 (m, 1H); 1.36 (d, J=7.2, 3H); 0.88 (d, J=6.7, 6H).

$^{13}$C-nmr (CDCl$_3$): δ=173.5, 169.3, 150.5, 144.4, 125.1, 72.1, 48.9, 43.0, 28.2, 19.5, 19.5, 18.9.

$C_{14}H_{20}N_2O_3$ (MW=264, Mass Spectroscopy (MH$^+$265))

Example 13

Synthesis of N-(phenylacetyl)-L-alanine zso-butyl ester

Following General Procedure B and using phenylacetyl chloride (Aldrich) and L-alanine iso-butyl ester hydrochloride (from Example B above), the title compound was prepared as a solid having a melting point of 45°–47° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=7.24–7.39 (m, 5H), 6.14 (d, 1H), 4.58 (t, J=7.3 Hz, 1H), 3.88 (m, 2H), 3.58 (s, 2H), 1.90 (m, 1H), 1.35 (d, J=7.2 Hz, 3H), 0.89 (d, J=6.7 Hz, 6H).

$^{13}$C-nmr (CDCl$_3$): δ=172.8, 170.4, 134.5, 129.3, 128.9, 127.2, 71.3, 48.1, 43.5, 27.5, 18.9, 18.8, 18.4.

$C_{15}H_{21}NO_3$ (MW=263.34, Mass Spectroscopy (MH$^+$ 264)).

Example 14

Synthesis of 2-[(3,4-dichlorophenyl)acetamido]butyric acid iso-butyl ester

Following General Procedure I above and using 3,4-dichlorophenylacetic acid (Aldrich) and iso-butyl 2-aminobutyrate (prepared following General Procedure J above) the title compound was prepared. The reaction was monitored by tlc on silica gel and purification was by filtration as described in the general procedure.

NMR data was as follows:

$^1$H-nmr (CDCl$_3$): δ=7.36 (m, 3H), 6.03 (bd, 1H), 4.54 (m, 1H), 3.87 (m, 2H), 3.49 (s, 2H), 1.93 (m, 2H), 1.72 (m, 1H), 0.88 (d, 6H), 0.80 (t, 3H).

Example 15

Synthesis of 2-[(3-methoxyphenyl)acetamido]butyric acid iso-butyl ester

Following General Procedure I above and using 3-methoxyphenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=6.75 (m, 4H), 5.93 (bd, 1H), 4.51 (m, 1H), 3.83 (m, 2H), 3.75 (s, 2H), 3.52 (s, 2H), 1.82 (m, 2H), 1.60 (m, 1H), 0.84 (d, 6H), 0.74 (t, 3H).

$C_{17}H_{25}NO_4$ (MW=307.39, Mass Spectroscopy (MH$^+$ 309)).

Example 16

Synthesis of 2-[(4nitrophenyl)acetamido]butyric acid iso-butyl ester

Following General Procedure I above and using 4-nitrophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=8.16 (d, 2H), 7.44 (d, 2H), 6.04 (bd, 1H), 4.55 (m, 1H), 3.86 (m, 2H), 3.66 (s, 2H), 1.86 (m, 2H), 1.67 (m, 1H), 0.85 (d, 6H), 0.81 (t, 3H).

C$_{16}$H$_{22}$N$_2$O$_5$ (MW=322.36, Mass Spectroscopy (MH$^+$ 323)).

Example 17

Synthesis of 2-[(3,4-methylenedioxyphenyl) acetanido]butyric acid iso-butyl ester Following General Procedure I above and using 3,4-(methylenedioxy)-phenyl acetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=6.72 (m, 3H), 5.92 (bd, 1H), 4.54 (m, 1H), 3.86 (m, 2H), 3.66 (s, 2H), 1.86 (m, 2H), 1.66 (m, 1H), 0.89 (d, 6H), 0.79 (t, 3H).

Example 18

Synthesis of 2-[(thien-3-yl)acetamido]butyric acid iso-butyl ester

Following General Procedure I above and using 3-thiopheneacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.37 (m, 1H), 7.16 (m, 1i), 7.04 (m, 1H), 6.05 (bd, 1H), 4.57 (m, 1H), 3.66 (s, 2H), 1.93 (m, 2H), 1.67 (m, 1H), 0.91 (d, 6H), 0.86 (t, 3H).

Example 19

Synthesis of 2-[(4-chlorophenyl)acetanido]butyric acid iso-butyl ester

Following General Procedure I above and using 4chlorophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.22 (m, 2H), 7.11 (m, 2H), 5.80 (m, 1H), 4.44 (m, 1H), 3.78 (m, 2H), 3.43 (s, 2H), 1.77 (m, 2H), 1.56 (m, 1H), 0.83 (d, 6H) 0.71 (t, 3H).

Example 20

Synthesis of 2-[(3-nitrophenyl)acetamido]butyric acid iso-butyl ester

Following General Procedure I above and using 3-nitrophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=8.15 (m, 2H), 7.65 (m, 1H), 6.08 (m, 1H), 4.46 (m, 1H), 3.92 (m, 2H), 3.68 (s, 2H), 1.91 (m, 2H), 1.75 (m, 1H), 0.98 (d, 6H) 0.71 (t, 3H).

Example 21

Synthesis of 2-[(2-hydroxyphenyl)acetamido]butyric acid iso-butyl ester

Following General Procedure I above and using 2-hydroxyphenylacetic acid (Aldrich) and iso-butyl 2-aminobutrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.14 (m, 1H), 7.01 (m, 1H), 6.93 (m, 1H), 6.79 (m, 1H), 6.46 (m, 1H), 4.51 (m, 1H), 3.87 (m, 2H), 3.57 (s, 2H), 2.01 (m, 2H), 1.75 (m, 1H), 0.89 (d, 6H), 0.85 (t, 3H).

Example 22

Synthesis of 2-[(2-naphthyl)acetamido]butyric acid iso-butyl ester

Following General Procedure I above and using 2-naphthylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.83 (m, 7H), 5.95 (m, 1H), 4.58 (m, 1H), 3.84 (m, 2H), 3.75 (s, 2H), 1.89 (m, 2H), 1.63 (m, 1H), 0.91 (d, 6H), 0.81 (t, 3H).

C$_{20}$H$_{25}$NO$_3$ (MW=327.42, Mass Spectroscopy (MH$^+$ 328)).

Example 23

Synthesis of 2-[(2,4dichlorophenyl)acetamido] butyric acid iso-butyl ester

Following General Procedure I above and using 2,4-dichlorophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.49 (m, 1H), 7.22 (m, 2H) 5.98 (m, 1H), 4.52 (m, 1H), 3.86 (m, 2H), 3.61 (s, 2H), 1.84 (m, 2H), 1.62 (m, 1H) 0.87 (d, 6H), 0.80 (t, 3H).

Example 24

Synthesis of 2-[(4-bromophenyl)acetamido]butyric acid iso-butyl ester

Following General Procedure I above and using 4-bromophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.43 (d, 2H), 7.19 (d, 2H) 5.85 (m, 1H), 4.51 (m, 1H), 3.81 (m, 2H), 3.47 (s, 2H), 1.84 (m, 2H), 1.61 (m, 1H) 0.84 (d, 6H), 0.76 (t, 3H).

C$_{16}$H$_{22}$NO$_3$Br (MW=356.26, Mass Spectroscopy (MH$^+$ 358)).

Example 25

Synthesis of 2-[(3-chlorophenyl)acetamido])butyric acid iso-butyl ester

Following General Procedure I above and using 3-chlorophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.25 (m, 3H), 7.12 (m, 1H) 5.80 (m, 1H), 4.52 (m, 1H), 3.86 (m, 2H), 3.50 (s, 2H), 1.87 (m, 2H), 1.67 (m, 1H) 0.88 (d, 6H), 0.77 (t, 3H).

C$_{16}$H$_{22}$NO$_3$Cl (MW=311.81 Mass Spectroscopy (MH$^+$ 313)).

Example 26

Synthesis of 2-1[(3fluorophenylacetanido]butyric acid iso-butyl ester

Following General Procedure I above and using 3-fluorophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.31 (m, 1H), 7.01 (m, 3H) 5.95 (m, 1H), 4.54 (m, 1H), 3.84 (m, 2H), 3.54 (s, 2H), 1.88 (m, 2H), 1.65 (m, 1H) 0.87 (d, 6H), 0.81 (t, 3H).

C$_{16}$H$_{22}$NO$_3$F (MW=295.35 Mass Spectroscopy (MH$^+$ 296)).

Example 27

Synthesis of 2-[(benzothiazol-4-yl)acetamido] butyric acid iso-butyl ester

Following General Procedure I above and using 4-benzothiazol-yl acetic acid (Chemservice) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.82 (m, 1H), 7.51–7.21 (m, 4H) 5.84 (m, 1H), 4.51 (m, 1H), 3.90 (s, 2H), 3.79 (m, 2H), 1.78 (m, 2H), 1.58 (m, 1H) 0.80 (d, 6H), 0.66 (t, 3H).

Example 28

Synthesis of 2-[(2-methylphenyl)acetamido]butyric acid iso-butyl ester

Following General Procedure I above and using 2-methylphenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.18 (m, 4H), 5.79 (m, 1H), 4.54 (m, 1H), 3.85 (m, 2H), 3.59 (s, 2H), 3.29 (s, 3H), 1.81 (m, 2H), 1.59 (m, 1H) 0.87 (d, 6H), 0.77 (t, 3H).

C$_{17}$H$_{25}$NO$_3$ (MW=291.39 Mass Spectroscopy (M+291)).

Example 29

Synthesis of 2-[(2-fluorophenyl)acetamido]butyric acid iso-butyl ester

Following General Procedure I above and using 2-fluorophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.28 (m, 1H), 7.09 (m, 3H) 6.03 (m, 1H), 4.54 (m, 1H), 3.87 (m, 2H), 3.57 (s, 2H), 1.89 (m, 2H), 1.64 (m, 1H) 0.88 (d, 6H), 0.80 (t, 3H).

Example 30

Synthesis of 2-[(4-fluorophenyl)acetamido]butyric acid iso-butyl ester

Following General Procedure I above and using 4-fluorophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.20 (m, 2H), 6.97 (m, 2H) 5.87 (m, 1H), 4.492 (m, 1H), 3.83 (m, 2H), 3.48 (s, 2H), 1.86 (m, 2H), 1.60 (m, 1H) 0.87 (d, 6H), 0.78 (t, 3H).

C$_{16}$H$_{22}$NO$_3$F (MW=295.35 Mass Spectroscopy (MH$^+$ 296)).

Example 31

Synthesis of 2-[(3-bromophenyl)acetamido]butyric acid iso-butyl ester

Following General Procedure I above and using 3-bromophenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.45 (m, 2H), 7.23 (m, 2H) 5.95 (m, 1H), 4.55 (m, 1H) 3.84 (m, 2H) 3.55 (s, 2H), 1.89 (m, 2H), 1.68 (m, 1H) 0.91 (d, 6H), 0.81 (t, 3H).

C$_{16}$H$_{22}$NO$_3$Br (MW=356.26 Mass Spectroscopy (M+357)).

Example 32

Synthesis of 2-[(3-trifluoromethylphenyl)acetamido] butyric acid iso-butyl ester Following General Procedure I above and using 3-trifluoromethyl-phenylacetic acid (Aldrich) and iso-butyl 2-aminobutyrate (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.52 (m, 1H), 7.47 (m, 2H) 6.01 (m, 1H), 4.56 (m, 1H), 3.86 (m, 2H), 3.61 (s, 2H), 1.84 (m, 2H), 1.62 (m, 1H) 0.87 (d, 6H), 0.80 (t, 3H).

C$_{17}$H$_{22}$NO$_3$F$_3$ (MW=345.36 Mass Spectroscopy (MH$^+$ 345)).

Example 33

Synthesis of 2-[(2-thienyl)acetamido]butyric acid isobutyl ester

Following General Procedure I above and using 2-thiopheneacetic acid (Aldrich) and iso-butyl 2-aminobutyrate (prepared following General Procedure J above), the tide compound was prepared. The reaction was monitored by tlc on silica gel and purification was by filtration as described in the general procedure.

NMR data was as follows:

$^1$H-nmr (CDCl$_3$): δ=6.89 (m, 3H), 6.07 (bd, 1H), 4.50 (m, 1H), 3.82 (m, 2H), 3.71 (s, 2H), 1.85 (m, 2H), 1.62 (m, 1H), 0.81 (d, 6H), 0.75 (t, 3H).

$C_{14}H_{21}NO_3S$ (MW=283.39, Mass Spectroscopy (MH$^+$ 284)).

Example 34

Synthesis of 2-(phenylacetamido)butyric acid iso-butyl ester

Following General Procedure H above and using phenylacetic acid (Aldrich) and iso-butyl 2-aminobutyrate (prepared following General Procedure J above), the title compound was prepared. The reaction was monitored by tlc on silica gel and purification was by chromatography on silica gel using 9:1 toluene:EtOAc as the eluant.

NMR data was as follows:

$^1$H-nmr (CDCl$_3$): δ=7.17–7.28 (m, 5H), 6.23 (bd, 1H), 4.51 (m, 1H), 3.86 (m, 2H), 3.54 (s, 2H), 1.87 (m, 2H), 1.62 (m, 1H), 0.87 (d, 6H), 0.78 (t, 3H).

$C_{16}H_{23}NO_3$ (MW=277.36, Mass Spectroscopy (MH$^+$ 277)).

Example 35

Synthesis of N-(phenylacetyl)valine 2-methylbutyl ester

Step A. Preparation of N-(phenylacetyl) valine

To a stirred solution of 5.15 g (44 mmol) of valine (Bachem) in 50 mL (100 mmol) of 2N NaOH cooled to 0° C. was added dropwise 5.3 mL (40 mmol) of phenylacetyl chloride (Aldrich). A colorless oil precipitated. The reaction mixture was allowed to warm to room temperature and stirred for 18 hours, washed with 50 mL diethyl ether, acidified to pH 2–3 with aqueous HCl. The white precipitate formed was filtered off, washed thoroughly with water, followed by diethyl ether to give 7.1 g (30 mmol, 69% yield) of the title compound.

NMR data was as follows:

$^1$H-nmr (DMSO-d$_6$): δ=12.63 (s, 1H), 8.25 (d, J=8.6 Hz, 1H), 7.27 (m, 5H), 4.15 (m, 1H), 3.56 (d, J=13.8 Hz, 1H), 3.47 (d, J=13.8 Hz, 1H), 2.05 (m, 1H), 0.87 (d, J=6.8, Hz, 3H), 0.84 (d, J=6.8 Hz, 3)

$^{13}$C-nmr (DMSO-d$_6$): δ=173.2, 170.4, 136.6, 129.0, 128.2, 126.3, 57.1, 41.9, 30.0, 19.2, 18.0

$C_{13}H_{17}NO_3$ (MW=235.29; Mass Spectroscopy (MH$^+$=236))

Step B. Synthesis of N-(phenylacetyl)valine 2-methylbutyl ester

Following General Procedure C and using the N-(phenylacetyl) valine prepared in Step A above and 2-methylbutan-1-ol (Aldrich), the title compound was prepared as a diastereomeric mixture. The reaction was monitored by tlc on silica gel and purification was by filtration as described in the general procedure.

NMR data was as follows:

$^1$H-nmr (CDCl$_3$): δ=7.25–7.40 (m, 5H), 5.95 (d, 1H), 4.56 (m, 1H), 3.84–4.00 (m, 2H), 3.61 (s, 2H), 2.10 (m, 1H), 1.68 (m, 1H), 1.38 (m, 1H), 1.15 (m 1H), 0.82–0.94 (m, 9H), 0.76 (d, 3H).

$^{13}$C-nmr (CDCl$_3$): δ=171.84, 171.81, 170.7, 134.6, 129.31, 129.27, 128.9, 127.3, 69.8, 57.0, 43.7, 33.9, 31.3, 25.9, 25.8,, 18.9, 17.4, 16.34, 16.27, 11.12, 11.07.

$C_{18}H_{27}NO_3$ (MW=305.42, Mass Spectroscopy (MH 306)).

Example 36

Synthesis of N-(phenylacetyl)-L-methionine iso-butyl ester

L-Methionine (0.129 g, 0.869 mmols) (Aldrich) was taken-up in dioxane (5.0 mL) and treated with a saturated solution of sodium bicarbonate (5.0 mL) followed by phenylacetyl chloride (Aldrich) (0.114 mL, 0.822 mmols). After stirring for 17 hours at room temperature the mixture was diluted with ethyl acetate, the layers separated and the aqueous layer acidified to pH 2 with 5N HCl. The crude product was extracted into ethyl acetate, dried over sodium sulfate, vacuum dried and used without further purification.

N-phenylacetyl-L-methionine (0.1285 g, 0.447 mmol) was dissolved in 3.0 mL dioxane and iso-butyl alcohol (0.2 mL) and treated with EDC (0.094 g, 0.492 mmol), and catalytic DMAP (0.015 g). After stirring for 17 hours at 23° C., the mixture was evaporated at reduced pressure to an oil, the residue was diluted in EtOAc and washed with 0.1 N HCl and saturated sodium bicarbonate. Chromatography on silica gel using 98:2 CHCl$_3$/MeOH as eluant provided the pure product.

NMR data was as follows:

$^1$H-nmr (CDCl$_3$): δ=7.4–7.23 (m, 5H), 6.14 (bd, 1H), 4.70 (m, 1H), 3.89 (d, 2H), 3.62 (s, 2H), 2.43 (m, 2H), 2.12 (m, 1H), 1.93 (m, 2H), 0.94 (d, 6H).

$C_{17}H_{25}NO_3S$ (MW=323.17, Mass Spectroscopy (M$^+$323)

Example 37

Synthesis of N-(phenylacetyl)-L-leucine iso-butyl ester

L-Leucine (Aldrich) (0.114 g, 0.869 mmols) was taken-up in dioxane (5.0 mL) and treated with a saturated solution of sodium bicarbonate (5.0 mL) followed by phenylacetyl chloride (Aldrich) (0.114 mL, 0.822 mmols). After stirring for 17 hours at room temperature the mixture was diluted with ethyl acetate, the layers separated and the aqueous layer acidified to pH 2 with 5N HCl. The crude product was extracted into ethyl acetate, dried over sodium sulfate, vacuum dried and used without further purification.

N-Phenylacetyl-L-leucine (0.0081 g, 0.038 mmol) was dissolved in 2.0 mL CHCl$_3$ (ETOH free) and iso-butyl alcohol (0.055 mL) and treated with P-EPC (100 mg, 0.87 milliequivalents). The mixture was rotated for 4 days, filtered through a plug of cotton and the filtrate evaporated at reduced pressure to an oil which was sufficiently pure for testing.

NMR data was as follows:

$^1$H-nmr (CDCl$_3$): δ=7.22 (m, 5H), 5.57 (d, 1H), 4.35 (m, 1H), 3.35 (m, 3H), 1.35 (m, 4H), 0.68 (m, 9H).

$C_{18}H_{27}NO_3$ (MW=305.40, Mass Spectroscopy (M+305)).

Example 38

Synthesis of N-[(3-chlorophenyl)acetyl]alanine 3-methylbut-2-enyl ester

Following General Procedure C above and using N-(3-chlorophenylacetyl alanine (from Example D above) and 3-methylbut-2-en-1-ol (Aldrich), the title compound can be prepared. The reaction was monitored by tlc on silica gel and purification was by liquid chromatography using 30% EtOAc/hexane as the eluant.

NMR data was as follows:

$^1$H-nmr (CDCl$_3$): δ=7.39–7.16 (m, 4H), 6.06 (bd, 1H), 5.38–5.29 (m, 1H), 4.63 (d, J=9Hz, 2H), 3.56 (s, 2H), 1.79 (s, 3H), 1.7 (s, 3H), 1.39 (d, J=9Hz, 3H).

Example 39

Synthesis of N-[(3-chlorophenyl)acetyl]alanine cyclopropylmethyl ester

Following General Procedure C above, and using N-(3-chlorophenylacetyl alanine (from Example D above) and cyclopropylmethanol (Aldrich), the title compound can be prepared. The reaction was monitored by tlc on silica gel and purification was by liquid chromatography using 3:7 EtOAc:hexane as the eluant.

NMR data was as follows:

$^1$H-nmr (CDCl): δ=7.2–7.1 (m, 4H), 6.09 (bs, 1H), 4.6 (dq, J=9 Hz, 1H), 3.96 (dd, J=9Hz, 2H), 3.59 (s, 2H), 1.2 (d, J=9Hz, 3H), 1.2–1.0 (m, 1H), 0.603–0.503 (m, 2H), 0.300–0.203 (m, 2H).

Example 40

Synthesis of N-[(3-chlorophenyl)acetyl]alanine 2thienylmethyl ester

Following General Procedure C above, and using N-(3-chlorophenylacetyl alanine (from Example D above) and 2-thiophenemethanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.37–6.97 (m, 7H), 5.97 (q, J=14 Hz, 2H), 4.6 (dq, J=9 Hz, 1H), 3.76 (s, 2H), 1.38 (d, J=9Hz, 3H).

Example 41

Synthesis of N-[(3-chlorophenyl)acetyl]alanine (1-methylcyclopropyl)methyl ester Following General Procedure C above, and using N-(3-chlorophenylacetyl alanine (from Example D above) and (1-methylcyclopropyl)methanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.6 (bd, J=9 Hz, 1H), 3.86 (q, J=14 Hz, 2H), 3.4 (s, 2H), 2.29 (q, J=9 Hz, 1H), 1.3 (d, J=9Hz, 3H), 1.03 (s, 3H), 0.5–0.4 (m, 2H), 0.4–0.28 (m, 2H).

Example 42

Synthesis of N-[(3-chlorophenyl)acetyl]alanine 3-thienylmethyl ester

Following General Procedure C above, and using N-(3-chlorophenylacetyl alanine (from Example D above) and 3-thiophenemethanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.03 (bd, J=9 Hz, 1H), 7.56–7.5 (m, 1H), 7.47 (bs, 1H), 7.4–7.17 (m, 4H), 7.06 (d, J=9 Hz, 1H), 5.1 (s, 2H), 4.3 (dq, 1H), 1.3 (d, J=9 Hz, 3H).

Example 43

Synthesis of N-[(3-chlorophenyl)acetyl]alanine 2-methylcyclopentyl ester

Following General Procedure C above, and using N-(3-chlorophenylacetyl alanine (from Example D above) and 2-methylcyclopentanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.39–7.16 (m, 4H), 6.3 (bd, 1H), 4.79–4.7 (m, 1H), 4.6–4.25 (m, J=9 Hz, 1H), 3.577 (s, 2H), 2.09–1.8 (m, 2H), 1.74–1.6 (m, 2H), 1.39 (dd, J=9 Hz, 3H), 1.2 (dt, J=9 Hz, 1H), 0.979 (dd, J=9 Hz, 2H)

$C_{17}H_{22}NO_3Cl$ (MW=323.82, Mass Spectroscopy (MH$^+$ 323).

Example 44

Synthesis of N-[(3-chlorophenyl)acetyl]alanine 2-methylprop-2-enyl ester

Following General Procedure C above, and using N-(3-chlorophenylacetyl alanine (from Example D above) and 2-methylprop-2-en-1-ol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.39–7.16 (m, 4H), 6.03 (bs, 1H), 4.77 (s, 2H), 4.7–4.29 (m, 3H), 2.59 (s, 2H), 1.73 (s, 3H), 1.43 (d, J=9 Hz, 3H) $C_{15}H_{18}NO_3Cl$ (MW=295.76, Mass Spectroscopy (MH$^+$295)).

Example 45

Synthesis of N-[(3-chlorophenyl)acetyl]alanine cyclohex-2enyl ester

Following General Procedure C above, and using N-(3-chlorophenylacetyl alanine (from Example D above) and cyclohex-2-en-1-ol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.6 (bd, J=9 Hz, 1H), 7.4–7.2 (m, 4H), 6.0–5.8 (m, 1H), 5.7–5.5 (m, 1H), 5.1 (bs, 1H), 4.134.29 (m, 1H), 3.5 (s, 2H), 2.1–1.9 (m, 2H), 1.8–1.69 (m, 1H), 1.69–1.49 (m, 4H), 1.3 (dd, J=9 Hz, 3H)

$C_{17}H_{20}NO_3Cl$ (MW=321.8, Mass Spectroscopy (MH$^+$ 321.2)).

Example 46

Synthesis of N-[(2-phenylbenzoxazol-5-yl)acetyl] alanine iso-butyl ester

Following General Procedure I above, and using 5-(2-phenylbenzoxazol)-yl-acetic acid (CAS# 62143–69–5) and alanine iso-butyl ester (prepared following General Procedure J above), the title compound was prepared.

NMR data was as follows:

$^1$H-nmr (CDCl$_3$): δ=8.24 (m, 3H), 7.68 (m, 1H), 7.51 (m, 5H), 6.04 (m, 1H), 4.58 (m, 1H), 3.85 (m, 2H), 3.68 (s, 2H), 1.9 (m, 1H), 1.35 (d, 3H), 0.87 (d, 6H).

C$_{22}$H$_{24}$N$_2$O$_4$ (MW=380, Mass Spectroscopy (MH$^+$381)).

Example 47

Synthesis of N-[(3-methylthiophenyl)acetyl]alanine iso-butyl ester

Following General Procedure I above, and using 3-methylthiophenylacetic acid (CAS# 18698–73–2) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.14 (m, 2H), 7.01 (m, 1H), 4.56 (m, 1H), 3.88 (m, 2H), 3.54 (s, 2H), 2.46 (s, 3H), 1.89 (m, 1H), 1.35 (d, 3H) 0.85 (d, 6H).

C$_{16}$H$_{23}$NO$_3$S (MW=309, Mass Spectroscopy (MH$^+$310)).

Example 48

Synthesis of N-4-[(2-furyl)acetyl]alanine iso-butyl ester

Following General Procedure I above, and using 2-furylacetic acid (CAS# 2745–26–8) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.36 (m, 1H), 6.34 (m, 1H), 6.21 (m, 1H), 4.56 (m, 1H), 3.91 (m, 2H), 3.61 (s, 2H), 1.92 (m, 1H), 1.38 (d, 3H) 0.89 (d, 6H).

C$_{13}$H$_{19}$NO$_4$ (MW=253, Mass Spectroscopy (MH$^+$254)).

Example 49

Synthesis of N-[(benzofuran-2-yl)acetyl]alanine iso-butyl ester

Following General Procedure I above, and using benzofuran-2-ylacetic acid (Maybridge) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.51 (m, 1H), 7.44 (m, 1H), 7.25 (m, 2H), 6.67 (s, 1H), 4.60 (m, 1H), 3.87 (m, 2H), 3.77 (s, 2H), 1.88 (m, 1H), 1.38 (d, 3H), 0.87 (d, 6H).

C$_{17}$H$_{21}$NO$_4$ (MW=303, Mass Spectroscopy (MH$^+$304)).

Example 50

Synthesis of N-[(benzothiophen-3-yl)acetyl]alanine iso-butyl ester

Following General Procedure I above, and using thianaphthen-3-ylacetic acid (Lancaster) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.89 (m, 1H), 7.76 (m, 1H), 7.38 (m, 3H), 6.07 (m, 1H), 4.57 (m, 1H), 3.92 (m, 2H), 3.82 (s, 4H), 1.84 (m, 1H), 1.32 (d, 3H) 0.85 (d, 6H).

C$_{17}$H$_{21}$NO$_3$S (MW 319, Mass Spectroscopy (MH$^+$320)).

Example 51

Synthesis of N-[(2-chloro-5-thienyl)acetyl]alanine iso-butyl ester

Following General Procedure I above, and using 5-chloro-2-thienyl)acetic acid (CAS# 13669–19–7) and alanine isobutyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=6.77 (m, 1H), 6.68 (d, 1H), 6.31 (bm, 1H), 4.59 (m, 1H), 3.91 (m, 2H), 3.38 (s, 2H), 1.90 (m, 1H), 1.39 (d, 3H) 0.89 (d, 6H).

C$_{13}$H$_{18}$NO$_3$SCl (MW=303, Mass Spectroscopy (MH$^+$ 303)).

Example 52

Synthesis of N-[(3-methylisoxazol-5-yl)acetyl]alanine iso-butyl ester

Following General Procedure I above, and using (3-methyl-isoxazol-5-yl)acetic acid (CAS# 19668–85–0) and alanine iso-butyl ester (prepared following General Procedure I above), the title compound was prepared. The reaction was monitored by tlc on silica gel and purification was by filtration as described in the general procedure.

NMR data was as follows:

$^1$H-nmr (CDCl$_3$): δ=6.07 (s, 2H), 4.56 (m, 1H), 3.92 (m, 2H), 3.68 (s, 2H), 2.29 (s, 3H), 1.94 (m, 1H), 1.89 (d, 3H) 0.91 (d, 6H).

C$_{13}$H$_{20}$N$_2$O$_4$ (MW 268, Mass Spectroscopy (MH$^+$269)).

Example 53

Synthesis of N-[(2-phenylthiothienyl)acetyl]alanine iso-butyl ester

Following General Procedure I above, and using (2-phenylthiothienyl)acetic acid and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.21–7.11 (m, 6H), 6.92 (d, 1H), 4.56(m, 1H), 3.87 (m, 2H), 3.72 (s, 2H), 1.94 (m, 1H), 1.38 (d, 3H) 0.89 (d, 6H).

C$_{19}$H$_{23}$NO$_3$S$_2$ (MW=377, Mass Spectroscopy (MH$^+$ 378)).

Example 54

Synthesis of N-[(6-methoxybenzothiophen-2-yl) acetyl]alanineiso-butyl ester

Following General Procedure I above, and using (6-methoxythianaphthen-2-yl)acetic acid and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.59 (d, 1H), 7.33 (d, 1H), 7.16 (s, 1H), 7.03 (dd, 1H), 4.56 (m, 1H), 3.87(s, 3H), 3.84 (m, 2H), 3.76 (s, 2H),1.85 (m, 1H), 1.30 (d, 3H) 0.86 (d, 6H).

C$_{18}$H$_{23}$NO$_4$S (MW=349, Mass Spectroscopy (MH$^+$350)).

Example 55

Synthesis of N-[(3-phenyl-1,2,4-thiadiazol-5-yl) acetyl]alanine iso-butyl ester

Following General Procedure I above, and using (3-phenyl-1,2,4-thiadiazol-5-yl)acetic acid (CAS# 90771–06–5) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.47 (m, 5H), 4.66 (m, 1H), 4.16 (s, 2H), 3.91 (m, 2H), 1.93 (m, 1H), 1.48 (d, 3H) 0.93 (d, 6H).

C$_{17}$H$_{21}$N$_3$O$_3$S (MW=347, Mass Spectroscopy (MH$^+$348)).

Example 56

Synthesis of N-[2-phenyloxazol-4-yl)acetyl]alanine iso-butyl ester

Following General Procedure I above, and using (2-phenyloxazol-4-yl)acetic acid (CAS# 22086–89–1) and alanine iso-butyl ester (prepared following General Procedure J above), the title compound was prepared. The reaction was monitored by tlc on silica gel and purification was by filtration as described in the general procedure.

Example 57

Synthesis of N-[(3-methylphenyl)acetyl]alanine iso-butyl ester

Following General Procedure I above, and using 3-methylphenylacetic acid (Aldrich) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.21 (m, 1H), 7.07 (m, 3H), 4.54 (m, 1H), 3.83 (m, 2H), 3.52 (s, 2H), 2.35 (s, 3H), 1.87 (m, 1H), 1.32 (d, 3H), 0.88 (d, 6H).

C$_{16}$H$_{23}$NO$_3$ (MW=277, Mass Spectroscopy (MH$^+$278)).

Example 58

Synthesis of N-[(2,5-difluorophenyl)acetyl]alanine iso-butyl ester

Following General Procedure I above, and using 2,5-difluorophenylacetic acid (Aldrich) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.08–6.94 (m, 3H), 4.57 (m, 1H), 3.91 (m, 2H), 3.56 (s, 2H), 1.92 (m, 1H), 1.41 (d, 3H) 0.91 (d, 6H).

C$_{15}$H$_{19}$NO$_3$F$_2$ (MW=299, Mass Spectroscopy (MH$^+$ 300)).

Example 59

Synthesis of N-[(3,5-diflurophenyl)acetyl]alanine iso-butyl ester

Following General Procedure I above, and using 3,5-difluorophenylacetic acid (Aldrich) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=6.81 (m, 2H), 6.74 (m, 1H), 6.06 (m, 1H), 4.57 (m, 1H), 3.92 (m, 2H), 3.51 (s, 2H), 1.94 (m, 1H), 1.36 (d, 3H) 0.87 (d, 6H).

C$_{15}$H$_{19}$NO$_3$F$_2$ (MW=299, Mass Spectroscopy (MI+300)).

Example 60

Synthesis of N-[(3-thienyl)acetyl]alanine iso-butyl ester

Following General Procedure I above, and using 3-thiopheneacetic acid (Aldrich) and alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.33 (m, 1H), 7.14 (m, 1H), 7.01 (m, 1H), 6.09 (m, 1H), 4.58 (m, 1H), 3.88 (m, 2H), 3.60 (s, 2H), 1.91 (m, 1H), 1.37 (d, 3H) 0.92 (d, 6H).

Optical Rotation: [α]$_{23}$ –52 (c 1 MeOH) @ 589 nm.

C$_{13}$H19NO$_3$S (MW=269, Mass Spectroscopy (MH$^+$ 269)).

Example 61

Synthesis of N-[(4-methylphenyl)acetyl]alanine iso-butyl ester

Following General Procedure I above, and using 4-methylphenylacetic acid (Aldrich) and L-alanine iso-butyl ester (prepared following General Procedure J above), the title compound was prepared. The reaction was monitored by tlc on silica gel and purification was by filtration as described in the general procedure.

NMR data was as follows:

$^1$H-nmr (CDCl$_3$): δ=7.11 (s, 4H), 5.93 (m, 1H), 4.58 (m, 1H), 3.88 (m, 2H), 3.54 (s, 2H), 2.33 (s, 3H), 1.89 (m, 1H), 1.32 (d, 3H), 0.89 (d, 6H). C$_{16}$H$_{23}$NO$_3$ (MW=277.35, Mass Spectroscopy (MH$^+$278)).

Example 62

Synthesis of N-(phenylacetyl)-1-alanine S-1-(methoxycarbonyl) iso-butyl ester

Following General Procedure K and using (S)-(+)-2-hydroxy-2-methylbutyric acid (Aldrich) in place of the amino acid, methyl (S)-(+)-2-hydroxy-2-methylbutyrate was prepared.

Methyl (S)-(+)-2-hydroxy-2-methylbutyrate was then coupled with carbobenzyloxy-L-alanine (Aldrich) using General Procedure E to provide carbobenzyloxy-L-alanine S-1-(methoxycarbonyl) iso-butyl ester.

Carbobenzyloxy-L-alanine S-1-(methoxycarbonyl) iso-butyl ester (1.0 g) was then dissolved in 20 mL of methanol and 6N HCl (0.5 mL) and 10% palladium on carbon (0.1 g) were added. This reaction mixture was hydrogenated at 40 psi of hydrogen on a Parr apparatus for 5 hours at room temperature and then filtered through a pad of Celite. The filtrate was concentrated at reduced pressure to provide L-alanine S-1-(methoxycarbonyl) iso-butyl ester hydrochloride (98% yield).

L-Alanine S-1-(methoxycarbonyl) iso-butyl ester hydrochloride was then coupled to phenylacetic acid using General Procedure G to provide the title compound.

NMR data was as follows:

$^1$H-nmr (CDCl$_3$): δ=7.35–7.20 (m, 5H), 6.22 (bd, 1H), 4.83 (d, 1H), 4.65 (p, 1H), 3.68 (s, 3H), 3.55 (s, 2H), 2.21 (m, 1H), 1.40 (d, 3H), 0.97 (d, 3H), 0.93 (d, 3H).

$^{13}$C-nmr (CDCl$_3$): δ=173.25, 171.18, 170.22, 135.11, 129.94, 129.50, 127.88, 52.67, 48.49, 43.98, 30.53, 19.21, 18.75, 17.58.

Example 63

Synthesis of N-[(3-nitrophenyl)acetyl]-L-alanine iso-butyl ester

Following General Procedure H above and using 3-nitrophenylacetic acid (Aldrich) and L-alanine iso-butyl ester hydrochloride (from Example B above), the title compound was prepared. The reaction was monitored by tlc on silica gel and purification was by recrystallization from butyl chloride.

NMR data was as follows:

$^1$H-nmr (CDCl$_3$): δ=8.17 (m, 2H), 7.68 (d, 1H), 7.52 (t, 1H), 6.18 (m, 1H), 4.48 (m, 1H), 3.94 (m, 2H), 3.67 (s, 2H), 1.93 (m, 1H), 1.42 (d, 3H), 0.91 (d, 3H).

Optical Rotation: [α]$_{23}$ –49 (c 5, MeOH).

Example 64

Synthesis of N-[(3,5-difluorophenyl)acetyl]alanine ethyl ester

Following General Procedure G and using 3,5-difluorophenylacetic acid (Aldrich) and alanine ethyl ester (Aldrich), the title compound was prepared as a solid with a melting point of 93°–95° C. The reaction was monitored by tlc on silica gel (Rf=0.8 in EtOAC) and purification was by chromatography on silica gel using EtOAc as the eluant followed by recrystallization from 1-chlorobutane.

NMR data was as follows:

$^1$H-nmr (DMSO-d$_6$): δ=1.30 (d, 3H); 3.52 (s, 2H).

C$_{13}$H$_{15}$NO$_3$F$_2$ (MW=271.26, Mass Spectroscopy (MH$^+$ 271)).

Example 65

Synthesis of N-[(3-nitrophenyl)acetyl]methionine ethyl ester

Following General Procedure G above and using 3-nitrophenylacetic acid (Aldrich) and methionine ethyl ester hydrochloride (Aldrich), the title compound was prepared. The reaction was monitored by tlc on silica gel and purification was by recrystallization from butyl chloride.

NMR data was as follows:

$^1$H-nmr (CDCl$_3$): δ=8.18 (s, 1H), 8.15 (d, 1H) 7.66 (d, 1H), 7.48 (t, 1H), 6.30 (m, 1H), 4.67 (m, 1H), 4.21 (t, 2H), 3.67 (s, 2H), 2.47 (t, 2H), 2.12 (m, 2 H), 2.08 (s, 3H), 1.27 (t, 3H).

Optical Rotation: [α]$_{23}$ –30 (c 5, MeOH).

Example 66

Synthesis of N-[(3-chlorophenyl)acetyl]alanine iso-butyl ester

Following General Procedure G above and using 3-chlorophenylacetic acid (Aldrich) and alanine iso-butyl ester (prepared following General Procedure J above), the title compound was prepared. The reaction was monitored by tlc on silica gel.

NMR data was as follows:

$^1$H-nmr (CDCl$_3$): δ=7.29 (m, 3H), 7.18 (m, 1H), 6.0 (m, 1H), 4.56 (m, 1H), 3.89 (m, 2H), 3.53 (s, 2H), 1.91 (m, 1H), 1.39 (d, 3 H), 0.91 (d, 3H).

Optical Rotation: [α]$_{23}$ –45 (c 5, MeOH).

C$_{15}$H$_{20}$NO$_3$Cl (MW=297.78, Mass Spectroscopy (MH$^+$ 297)).

Example 67

Synthesis of N-[(3-chlorophenyl)acetyl]alanine 2(N, N-dimethylamino)ethyl ester

Following General Procedure C above, and using N-(3-chlorophenylacetyl)alanine (from Example D above) and 2-(N,N-dimethyl amino) ethanol (Aldrich), the title compound can be prepared. The reaction was monitored by tlc on silica gel and purification was by liquid chromatography using 0.1:2:0.79 NH$_4$OH:EtOH:CHCl$_3$ as the eluant.

NMR data was as follows:

$^1$H-nmr (CDCl$_3$): 7.37 (s, 1H), 7.33–7.2 (m, 3H), 4.675–4.6 (m, 1H), 4.5–4.37 (m, 1H), 4.25–4.13 (m, 1H), 3.6 (d, J=7 Hz, 2H), 2.86 (bs, 2H), 2.3 (s, 6H), 1.23 (d, J=9 Hz, 3H).

C$_{15}$H$_{21}$N$_2$O$_3$Cl (MW=313.799, Mass Spectroscopy (M+313)).

Example 68

Synthesis of 2-[(3,5-dichlorophenyl)acetamido] hexanoic acid methyl ester

Following General Procedure F above, an using 3,5-dichlorophenylacetic acid (from Example C above) and L-norleucine methyl ester hydrochloride (Bachem), the title compound was prepared as a solid having a melting point of 77°–78° C. The reaction was monitored by tlc on silica gel (Rf=0.70 in 40% EtOAC/hexanes) and purification was by flash chromatography on silica gel using 40% EtOAc/hexanes as the eluant.

NMR data was as follows:

$^1$H-nmr (CDCl$_3$): δ=7.20 (s), 7.18 (s), 6.6 (m), 4.55 (m), 3.7 (s), 3.5 (s), 3.4 (s), 2.0 (s), 1.8 (m), 1.6 (m), 1.2 (m), 0.8 (t).

$^{13}$C-nmr (CDCl$_3$): δ=173.54, 169.67, 138.43, 135.72, 128.33, 128.07, 78.04, 77.62, 77.19, 53.04, 52.90, 43.14, 32.57, 27.87, 22.81, 14.41.

Example 69

Synthesis of N-[(3,5-dichlorophenyl)acetyl]-L-alanine iso-butyl ester

Following General Procedure F above, and using 3,5-dichlorophenylacetic acid (from Example C above) and L-alanine iso-butyl ester hydrochloride (from Example B above), the title compound was prepared as a solid having a melting point of 115°–116° C. The reaction was monitored by tlc on silica gel (Rf=0.40 in 3% methanol/dichloromethane) and purification was by flash chromatography on silica gel using 3% methanol/dichloromethane as the eluant.

NMR data was as follows:

$^1$H-nmr (CDCl$_3$): δ=7.27 (d, J=2 Hz, 1H), 7.19 (s, 2H), 6.22 (d, J=6 Hz, 1H), 4.59 (quint., J=7 Hz, 1H), 3.9 (q, J=4 Hz, 2H), 3.5 (s, 2H), 1.9 (m, 1H), 1.4 (d, J=7 Hz, 3H), 0.91 (d, J=7 Hz, 6H).

$^{13}$C-nmr (CDCl$_3$): δ=173.45, 169.37, 138.31, 135.75, 128.39, 128.11, 78.04, 77.61, 77.19, 72.19, 54.03, 48.97, 43.12, 28.24, 19.52, 19.49, 19.09.

C$_{15}$H$_{19}$NO$_3$Cl$_2$ (MW=331.9, Mass Spectroscopy (MH$^+$ 332)).

Example 70

Synthesis of N-(cyclohexylacetyl)-L-alanine iso-butyl ester

Following General Procedure B above, and using cyclohexylacetic acid (Aldrich) and L-alanine iso-butyl ester hydrochloride (from Example B above), the title compound was prepared as a solid having a melting point of 92° C.–93° C. The reaction was monitored by tlc on silica gel (Rf=0.39 in 1:3 EtOAc:hexane) and purification was by extraction with Et$_2$O followed by washes with aqueous K$_2$CO$_3$ and aqueous HCl.

NMR data was as follows:

$^1$H-nmr (CDCl$_3$): δ=0.93 (d, J=6.7 Hz, 6H), 0.85–1.01 (m, 2H), 1.05–1.35 (m, 3H), 1.40 (d, J=7.1 Hz, 3H), 1.60–1.85 (m, 6H), 1.95 (m, 1H), 2.06 (d, J=7.0 Hz, 2H), 3.92 (m, 2H), 4.61 (m, 1H), 6.08 (bd, 1H).

$^{13}$C-nmr (CDCl$_3$): δ=18.7, 18.9, 26.0, 26.1, 27.6, 33.0, 35.3, 44.6, 47.9, 71.4, 171.8, 173.3.

C$_{15}$H$_{27}$NO$_3$ (MW=269.39, Mass Spectroscopy (MH$^+$ 270)).

Example 71

Synthesis of N-(cyclopentylacetyl)-L-alanine iso-butyl ester

Following General Procedure B above, and using cyclopentylacetic acid (Aldrich) and L-alanine iso-butyl ester hydrochloride (from Example B above), the title compound was prepared as a solid having a melting point of 62° C.–64° C. The reaction was monitored by tlc on silica gel (Rf=0.37 in 1:3 EtOAc:hexane) and purification was by extraction with Et$_2$O followed by washes with aqueous K$_2$CO$_3$ and aqueous HCl.

NMR data was as follows:

$^1$H-nmr (CDCl$_3$):=0.87 (d, J=6.8 Hz, 6H), 1.01–1.17 (m, 2H), 1.34 (d, J=7.2 Hz, 3H), 1.40–1.62 (m, 4H), 1.70–1.83 (m, 2H), 1.89 (m, 1H), 2.15 (m, 3H), 3.86 (m, 2H), 4.55 (m, 1H), 6.30 (d, J=7.1 Hz, 1H).

$^{13}$C-nmr (CDCl$_3$): δ=18.4, 18.78, 18.80, 24.8 (very high), 27.5, 32.27, 32.32, 36.9, 42.5, 47.7, 71.2, 172.2, 173.2.

Elemental Analysis-Calc (%): C, 65.85; H, 9.87; N, 5.49; Found (%): C, 66.01; H, 10.08; N, 5.49.

C$_{14}$H$_{25}$NO$_3$ (MW=255.36, Mass Spectroscopy (MH$^+$ 256)).

Example 72

Synthesis of N-[(cyclohex-1-enyl)acetyl]-L-alanine iso-butyl ester

Following General Procedure B above, and using cyclohex-1-enyl acetic acid (Alfa) and L-alanine iso-butyl ester hydrochloride (from Example B above), the title compound was prepared as a solid having a melting point of 49° C.–51° C. The reaction was monitored by tlc on silica gel (Rf=0.40 in 1:3 EtOAc:hexane) and purification was by extraction with Et$_2$O followed by washes with aqueous K$_2$CO$_3$ and aqueous HCl.

NMR data was as follows:

$^1$H-nmr (CDCl$_3$): δ=0.91 (d, J=4.5 Hz, 3H), 0.93 (d, J=6.7 Hz, 3H), 1.40 (d, J=7.2 Hz, 3H), 1.52–1.70 (m, 4H), 1.97 (m, 3H), 2.06 (bs, 2H), 2.89 (s, 2H), 3.92 (m, 2H), 4.59 (m, 1H), 5.65 (s, 1H), 6.33 (d, J=6.6 Hz, 1H).

$^{13}$C-nmr (CDCl$_3$): δ=18.7, 18.91, 18.93, 21.9, 22.7, 25.3, 27.6, 28.3, 46.1, 47.9, 71.4, 127.1, 132.5, 170.6, 173.1.

Elemental Analysis-Calc (%): C, 67.38; H, 9.42; N, 5.24; Found (%): C, 67.34; H, 9.54; N, 5.16.

C$_{15}$H$_{25}$NO$_3$ (MW=267.37, Mass Spectroscopy (MH$^+$ 268)).

Example 73

Synthesis of N-[(3-chlorophenyl)acetyl]alanine 3-methylbut-2-enyl thioester

Following General Procedure C above, and using N-[(3-chlorophenyl)acetyl] alanine and 3-methyl-2-butene thioester (TCI), the title compound can be prepared. The reaction was monitored by tlc on silica gel and purification was by liquid chromatography using 3:7 EtOAc:Hexane as the eluant.

NMR data was as follows:

$^1$H-nmr (DMSO-d$_6$): δ=5.2–5.075 (m, 1H), 4.37 (dq, J=9 Hz, 1H), 3.56 (s), 3.43 (d, J=12 Hz, 2H), 1.266 (d, J=12 Hz, 6H) 1.3 (d, J=9 Hz, 3H).

C$_{16}$H$_{20}$NO$_2$ClS (MW=325.86, Mass Spectroscopy (M+325)).

Example 74

Synthesis of N-[(2-phenyl)-2-fluoroacetyl]alanine ethyl ester

Following General Procedure F above, and using α-fluorophenyl acetic acid (Aldrich) and alanine ethyl ester (Aldrich), the title compound was prepared. The reaction was monitored by tlc on silica gel (Rf=0.75 in 1:1 EtOAc:hexane) and purification was by chromatography on silica gel using 1:2 ethyl acetate/hexanes as the eluent.

NMR data was as follows:

$^1$H-nmr (DMSO-d$_6$): δ=1.14 (q, 3H), 1.34 (d, 3H), 4.07 (m, 2H), 4.33 (m, 1H), 5.84 (d, 1H), 6.01 (d, 1H), 7.40–7.55 (m, 5H), 8.87 (m, 1H).

C$_{13}$H$_{16}$NO$_3$F (MW=253.27, Mass Spectroscopy (MH$^+$ 253)).

Example 75

Synthesis of N-(3,5-difluorophenylacetyl)-L-phenylglycine methyl ester

Following General Procedure F above, and using 3,5-difluorophenylacetic acid (Aldrich) and L-phenylglycine methyl ester hydrochloride (Bachem), the title compound was prepared.

NMR data was as follows:

$^1$H-nmr (CDCl$_3$): δ=7.4–7.3 (m, 5H), 6.9–6.7 (m, 3H), 6.55 (d 1H, 7.1 Hz), 5.56 (d 1H 7 Hz), 3.72 (s 3H), 3.57 (s 2H)

$^{13}$C-nmr (CDCl$_3$): δ=197.6, 177.6, 171.8, 169.3, 136.7, 129.6, 129.3, 127.8, 113.0, 112.9, 112.7, 111.4, 103.8, 103.5, 65.1, 57.2, 53.5, 45.1, 43.3, 43.3

C$_{17}$H$_{15}$NO$_3$F$_2$ (MW=319.31, Mass Spectroscopy (MH +320)).

Example 76

Synthesis of N-(3,5-difluorophenylacetyl)-L-phenylglycine isobutyl ester

The 3,5-difluorophenylacetic acid (Aldrich) was EDC coupled to L-phenylglycine methyl ester hydrochloride (Bachem) via General Procedure F above.

The resulting compound was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous NaHCO, was added. The volume of the reaction mixture was reduced on a rotary evaporator until the excess alcohol was removed and then the remaining residue was taken up in ethyl acetate and additional water was added. The organic phase was washed with saturated aqueous NaCl and dried over $MgSO_4$. The solution was stripped free of solvent on a rotary evaporator, and the crude product residue was then further purified by chromatography.

NMR data was as follows:

$^1$H-nmr (CDCl$_3$): δ=7.35–7.3 (m 5H), 6.8–6.7 (m 3H) 6.60 (d 1H, 7 Hz), 5.55 (d 1H 7.1 Hz), 3.9 (m 2H), 3.60 (s 2H), 1.85 (m 1H 7 Hz), 0.8 (q 6H 7 Hz)

$^{13}$C-nmr (CDCl$_3$): δ=171.3, 169.3, 165.4, 138.5, 137.0, 129.5, 129.2, 127.6, 113.1, 113.0, 112.8, 112.7, 103.8, 103.5, 103.2, 75.5, 57.2, 43.4, 43.3, 28.2, 19.3

$C_{20}H_{21}NO_3F_2$ (MW=361.39, Mass Spectroscopy (MH +362)).

Example 77

Synthesis of N-(cyclopentylacetyl)-L-phenylglycine methyl ester

Following General Procedure D above, and using cyclopentylacetic acid (Aldrich) with L-phenylglycine methyl ester hydrochloride (Bachem) the title compound was prepared.

NMR data was as follows:

$^1$H-nmr (CDCl$_3$): δ=7.35 (s, 5H), 6.44 (bd, 1H), 5.6 (d, 1H), 3.72 (s, 3H), 2.24 (bs, 3H), 1.9–1.4 (m, 6H), 1.2–1.05 (m, 2H)

$^{13}$C-nmr (CDCl$_3$): δ=172.3, 171.7, 136.7, 129.0, 128.6, 127.3, 56.2, 52.7, 42.5, 36.9, 32.40, 32.38, 24.8

Example 78

Synthesis of N-(cyclopentylacetyl)-L-alanine methyl ester

Following General Procedure D above, and using cyclopentylacetic acid (Aldrich) with L-alanine methyl ester hydrochloride (Sigma) the title compound was prepared.

NMR data was as follows:

$^1$H-nmr (CDCl$_3$): δ=6.38 (d, 1H), 4.50 (m, 1H), 3.65 (s, 3H), 2.13 (bs, 3H), 1.80–1.00 (m (includes d at 1.30, 3H), 11H)

$^{13}$C-nmr (CDCl$_3$): δ=173.7, 172.5, 52.1, 47.6, 42.3, 36.8, 32.15, 32.14, 18.0

$C_{11}H_{19}NO_3$ (MW=213.28, Mass Spectroscopy (MH$^+$ 214)).

Example 79

Synthesis of N-(cyclopropylacetyl)-L-phenylglycine methyl ester

Following General Procedure D above, and using cyclopropylacetic acid (Aldrich) with L-phenylglycine methyl ester hydrochloride (Bachem), the title compound was prepared.

NMR data was as follows:

$^1$H-nmr (CDCl$_3$): δ=7.35 (m, 5H) 6.97 (bd, J=7.2 Hz, 1H) 5.59 (d, J=7.8 Hz, 1H), 3.71 (s, 3H), 2.17 (m, 2H), 1.05–0.95 (m, 1H), 0.62 (m, 2H), 0.02 (m, 2H)

$^{13}$C-nmr (CDCl$_3$): δ=171.9, 174.6, 136.6, 129.0, 128.5, 127.2, 56.1, 52.7, 41.0, 6.9, 4.37, 4.33

Example 80

Synthesis of N-(cyclopropylacetyl)-L-alanine methyl ester

Following General Procedure D above, and using cyclopropylacetic acid (Aldrich) with L-alanine methyl ester hydrochloride (Sigma), the title compound was prepared.

NMR data was as follows:

$^1$H-nmr (CDCl$_3$): δ=6.60 (d, 1H), 4.55 (m, 1H), 3.69 (s, 3H), 2.10 (m, 2H), 1.34 (d, 3H), 0.95 (m, 1H), 0.58 (m, 2H) 0.15 (m, 2H)

$^{13}$C-nmr (CDCl$_3$): δ=173.7, 172.3, 52.3, 47.7, 41.0, 18.2, 6.7, 4.27, 4.22

Example 81

Synthesis of N-[(3-nitrophenyl)acetyl]-L-methionine iso-butyl ester

Following General Procedure H above, and using nitrophenylacetic acid (Aldrich) and L-methionine (Aldrich), the title compound was prepared as a tan oil. The reaction was monitored by tlc on silica gel.

NMR data was as follows:

$^1$H-nmr (CDCl$_3$): δ=8.16 (m,2H) 7.67 (d, 1H) 7.32 (t, 1H), 6.31 (bd, 1H), 4.69 (m, 1H), 3.90 (d, 2H), 3.68 (s, 2H), 2.47 (t, 2H), 2.15 (m, 1H), 2.02 (s, 3H), 1.90 (m, 2H), 0.91 (d, 6H).

$C_{17}H_{24}N_2O_5S$ (MW=368.4, Mass Spectroscopy (MH$^+$ 368)).

Example 82

Cellular Screen for the Detection of Inhibitors of β-Amyloid Production

Numerous compounds of formula I above were assayed for their ability to inhibit β-amyloid production in a cell line possessing the Swedish mutation. This screening assay employed cells (K293=human kidney cell line) which were stably transfected with the gene for amyloid precursor protein 751 (APP751) containing the double mutation Lys$_{651}$Met$_{652}$ to Asn$_{651}$Leu$_{652}$ (APP751 numbering) in the manner described in International Patent Application Publication No. 94/10569[8] and Citron et al.[11]. This mutation is commonly called the Swedish mutation and the cells, designated as "293 751 SWE", were plated in Corning 96-well plates at 1.5–2.5×10$^4$ cells per well in Dulbecco's minimal essential media plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 μL of a compound of formula I (drug) containing media per well for a two hour pretreatment period and cells were incubated as above. Drug stocks were prepared in 100% dimethylsulfoxide such that at the final drug concentration used in the treatment, the concentration of dimethylsulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR at 1200 rpm for five minutes at room temperature to pellet cellular debris from the conditioned media. From each well, 100 μL of conditioned media or appropriate dilutions thereof were transferred into an ELISA plate precoated with antibody 266[13] against amino acids 13–28 of β-amyloid peptide as described in International Patent Application Publication No. 94/10569[8] and stored at 4° C. overnight. An ELISA assay employing labelled antibody 6C6[13] against amino acids 1–16 of β-amyloid peptide was run the next day to measure the amount of β-amyloid peptide produced.

Cytotoxic effects of the compounds were measured by a modification of the method of Hansen, et al.[12]. To the cells remaining in the tissue culture plate was added 25 μL of a 3,(4,5-dimethylthiazol-2-yl)2,5-diphenyltetrazolium bromide (MTT) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562nm}$ and the $OD_{650nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compounds were assayed for β-amyloid peptide production inhibition activity in cells using this assay. The results of this assay demonstrate that, each of the compounds within this invention tested reduced β-amyloid peptide production by at least 30% as compared to control.

Example 83

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) Nature 373:523–527]. Depending upon which compound is being tested, the compound is usually formulated at either 5 or 10 mg/ml. Because of the low solubility factors of the compounds, they may be formulated with various vehicles, such as corn oil (Safeway, South San Francisco, CA); 10% EtOH in corn oil (Safeway); 2-hydroxypropyl-β-cyclodextrin (Research Biochemicals International, Natick Ma.); and carboxy-methyl-cellulose (Sigma Chemical Co., St. Louis Mo.). Specifically, for example 141 the vehicle was carboxy-methyl-cellulose (Sigma).

The mice are dosed subcutaneously with a 26 gauge needle and 3 hours later the animals are euthanized via $CO_2$ narcosis and blood is taken by cardiac puncture using a 1 cc 25G ⅝" tuberculin syringe/needle coated with solution of 0.5 M EDTA, pH 8.0. The blood is placed in a Becton-Dickinson vacutainer tube containing EDTA and spun down for 15 minutes at 1500 xg at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/ml aprotinin, 5 mM EDTA, pH 8.0, 10 μg/ml leupeptin], thereby reducing the final concentration of guanidine to 0.5 M, before centrifugation at 16,000 xg for 20 minutes at 4° C. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1–40) and β-amyloid (aa 1–42) consists of two monoclonal antibodies (mAb) to β-amyloid. The capture antibody, 266[13], is specific to amino acids 13–28 of β-amyloid. The antibody 3D6[14], which is specific to amino acids 1–5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/ml (11 pM) and shows no cross-reactivity to the endogenous murine β-amyloid peptide at concentrations up to 1 ng/ml.

The configuration of the sandwich ELISA quantitating the level of β-amyloid (aa 1–42) employs the mAb 21F12[14] (which recognizes amino acids 33–42 of β-amyloid) as the capture antibody. Biotinylated 3D6 is also the reporter antibody in this assay which has a lower limit of sensitivity of ~125 pg/ml (28 pM).

The 266 and 21F12 capture mAbs are coated at 10 μg/ml into 96 well immunoassay plates (Costar, Cambidge Ma.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed ≧3 times with wash buffer between each step of the assay. The biotinylated 3D6, diluted to 0.5 μg/ml in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge Ma.), is added and allowed to react for 15 minutes, after which the enzymatic reaction is stopped with addition of 2 N $H_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5 gm/l thimerosal, 8.5 gm/l sodium chloride, 0.5 ml TritonX405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

From the foregoing description, various modifications and changes in the composition and method will occur to those skilled in the art. All such modifications coming within the scope of the appended claims are intended to be included therein.

What is claimed is:

1. A method for inhibiting β-amyloid peptide release and/or its synthesis in a cell which method comprises administering to such a cell an amount of a compound or a mixture of compounds effective in inhibiting the cellular release and/or synthesis of β-amyloid peptide wherein said compounds are represented by formula I:

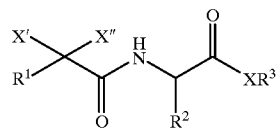

I wherein $R^1$ is selected from the group consisting of a) alkyl, alkenyl, alkcycloalkyl, phenyl—$(R)_m$—, naphthyl—$(R)_m$— wherein R is an alkylene group of from 1 to 8 carbon atoms and m is an integer equal to 0 or 1, cycloalkyl, ad cycloalkenyll, 3-pyridyl, 4-pyridyl and heteroaryl, other than 3- and 4-pyridyl, of 3 to 10 atoms and 1 to 4 heteroatoms selected fiom oxygen, sulfur and nitrogen wherein the heteroaryl group is optionally substituted with 1 to 3 substituents selected from the group consisting of alkyl, alkoxy, aryl, aryloxy, halo, nitro, thioalkoxy, and thioaryloxy with the proviso that for such heteroaryls when there is at least one nitrogen heteroatom, there is also at least one oxygen and/or sulfur heteroatom;

(b) a substituted phenyl group of formula II:

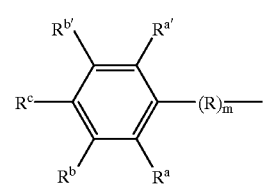

II wherein R is alkylene of from 1 to 8 carbon atoms,
m is an integer equal to 0 or 1,
$R^a$ and $R^{a'}$ are independently selected from the group consisting of hydrogen, hydroxy, fluoro and methyl;
$R^b$ and $R^{b'}$ are independently selected from the group consisting of hydrogen, alkyl, alkoxy, aryl, cyano, cycloalkyl, halo, heteroaryl, heterocyclic, nitro, trihalomethyl, thioalkoxy, thioaryloxy, thioheteroaryloxy, and —C(O)$R^4$ where $R^4$ is selected from the group consisting of alkyl, aryl, alkoxy and aryloxy; and
$R^c$ is selected from the group consisting of hydrogen, alkyl, aryl, cyano, halo, nitro, and where $R^b$ and $R^c$ are fused to form a methylenedioxy ring with the phenyl ring; and
when $R^b$ and/or $R^{b'}$ and/or $R^c$ is fluoro, chloro, bromo and/or nitro, then $R^a$ and/or $R^{a'}$ can also be chloro; and
(c) 1- or 2-naphthyl—$(R)_m$— substituted at the 5, 6, 7 and/or 8 positions with 1 to 4 substituents selected from the group consisting alkyl, alkoxy, halo, cyano, nitro, trihalomethyl, and thioalkoxy wherein R is an alkylene group of from 1 to 8 carbon atoms and m is an integer equal to 0 or 1;
$R^2$ is selected from the group consisting of hydrogen, alkyl, phenyl, alkylalkoxy, alkylthioalkoxy; and $R^3$ is selected from the group consisting of —(CH$_2$)$_n$ CR$^{10}$R$^5$R$^6$ wherein n is an integer equal to 0, 1 or 2, R$^5$ and R$^6$ are independently selected from hydrogen, alkyl, alkenyl, aryl, heteroaryl, heterocyclic, —NR$^7$R$^8$ where R$^7$ and R$^8$ are independently hydrogen or alkyl and —COOR$^9$ where R$^9$ is alkyl, and further wherein R$^5$ and R$^6$ can be joined to form a cycloalkyl group, a cycloalkenyl group, an aryl group, a heteroaryl group, and a heterocyclic group, and when R$^5$ and R$^6$ do not join to form an aryl or heteroaryl group, then R$^{10}$ is selected from hydrogen and alkyl with the proviso that when n is zero, then R$^{10}$ is hydrogen and when n is greater than zero and R$^5$ and R$^6$ are joined to form an aryl or heteroaryl group, then R$^{10}$ becomes a bond within that group;

X is oxygen or sulfur;

X' is hydrogen, hydroxy or fluoro;

X" is hydrogen, hydroxy or fluoro, or X' and X" together form an oxo group, and pharmaceutically acceptable salts thereof with the provisos that:

when R$^1$ is phenyl, R$^2$ is —CH(CH$_3$)CH$_2$CH$_3$, X is oxygen, and X' and X" are hydrogen, then R$^3$ is not —CH$_2$CH$_3$ or —CH$_2$CH(CH$_3$)$_2$ when R$^1$ is phenyl, R$^3$ is —CH$_2$CH(CH$_3$)$_2$, X is oxygen, and X' and X" are hydrogen, then R$^2$ is not —CH(CH$_3$)$_2$ when R$^1$ is 3,5-di(trifluoromethyl)phenyl, R$^2$ is methyl, X is oxygen, and X' and X" are hydrogen, then R$^3$ is not —CH$_2$CH(CH$_3$)$_2$, and when R$^1$ is —CH$_2$-phenyl, R$^3$ is —CH$_2$CH$_3$, X is oxygen, and X' and X" are hydrogen, then R$^2$ is not —CH$_2$CH(CH$_3$)$_2$.

2. A method for preventing the onset of AD in a patient at risk for developing AD which method comprises administering to said patient a pharmaceutical composition comprising a pharmaceutically inert carrier and an effective amount of a compound or a mixture of compounds of formula I:

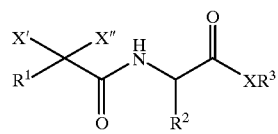

I wherein R$^1$ is selected from the group consisting of a) alkyl, alkenyl, alkcycloalkyl, phenyl—(R)$_m$—, naphthyl—(R)$_m$— wherein R is an alkylene group of from 1 to 8 carbon atoms and m is an integer equal to 0 or 1, cycloalkyl, and cycloalkenyl;

(b) a substituted phenyl group of formula II:

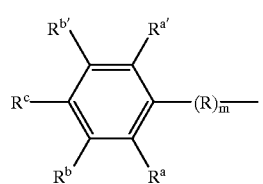

II wherein R is alkylene of from 1 to 8 carbon atoms, m is an integer equal to 0 or 1, R$^a$ and R$^{a"}$ are independently selected from the group consisting of hydrogen, hydroxy, fluoro and methyl;

R$^b$ and R$^{b'}$ are independently selected from the group consisting of hydrogen, alkyl, alkoxy, aryl, cyano, cycloalkyl, halo, heteroaryl, heterocyclic, nitro, trihalomethyl, thioalkoxy, thioaryloxy, thioheteroaryloxy, and —C(O)R$^4$ where R$^4$ is selected from the group consisting of alkyl, aryl, alkoxy and aryloxy; and R$^c$ is selected from the group consisting of hydrogen, alcyl, aryl, cyano, halo, nitro, and where R$^b$ and R$^c$ are fused to form a methylenedioxy ring with the phenyl ring; and when R$^b$ and/or R$^{b'}$ and/or R$^c$ is fluoro, chloro, bromo and/or nitro, then R$^a$ and/or R$^{a'}$ can also be chloro; and (c) 1- or 2-naphthyl—(R)$_m$— substituted at the 5, 6, 7 and/or 8 positions with 1 to 4 substituents selected from the group consisting alkyl, alkoxy, halo, cyano, nitro, trihalomethyl, and thioalkoxy wherein R is an alkylene group of from 1 to 8 carbon atoms and m is an integer equal to 0 or 1;

R$^2$ is selected from the group consisting of hydrogen, alkyl, phenyl, alkylalkoxy, alkylthioalkoxy; and R$^3$ is selected from the group consisting of —(CH$_2$)$_n$ CR$^{10}$R$^5$R$^6$ wherein n is an integer equal to 0, 1 or 2, R$^5$ and R$^6$ are independently selected from hydrogen, alkyl, alkenyl, aryl, heteroaryl, heterocyclic, —NR$^7$R$^8$ where R$^7$ and R$^8$ are independently hydrogen or alkyl and —COOR$^9$ where R$^9$ is alkyl, and further wherein R$^5$ and R$^6$ can be joined to form a cycloalkyl group, a cycloalkenyl group, an aryl group, a heteroaryl group, and a heterocyclic group, and when R$^5$ and R$^6$ do not join to form an aryl or heteroaryl group, then R$^{10}$ is selected from hydrogen and alkyl with the proviso that when n is zero, then R$^{10}$ is hydrogen and when n is greater than zero and R$^5$ and R$^6$ are joined to form an aryl or heteroaryl group, then R$^{10}$ becomes a bond within that group;

X is oxygen or sulfur;

X' is hydrogen, hydroxy or fluoro;

X" is hydrogen, hydroxy or fluoro, or X' and X" together form an oxo group, and pharmaceutically acceptable salts thereof with the provisos that:

when R$^1$ is phenyl, R$^2$ is —CH(CH$_3$)CH$_2$CH$_3$, X is oxygen, and X' and X" are hydrogen, then R$^3$ is not —CH$_2$CH$_3$ or —CH$_2$CH(CH$_3$)$_2$ when R$^1$ is phenyl, R$^3$ is —CH$_2$CH(CH$_3$)$_2$, X is oxygen, and X' and X" are hydrogen, then R$^2$ is not —CH(CH$_3$)$_2$ when R$^1$ is 3,5-di(trifluoromethyl)phenyl, R$^2$ is methyl, X is oxygen, and X' and X" are hydrogen, then R$^3$ is not —CH$_2$CH(CH$_3$)$_2$, and when R$^1$ is —CH$_2$-phenyl, R$^3$ is —CH$_2$CH$_3$, X is oxygen, and X' and X" are hydrogen, then R$^2$ is not —CH$_2$CH(CH$_3$)$_2$.

3. A method for treating a patient with AD in order to inhibit further deterioration in the condition of that patient which method comprises administering to said patient a pharmaceutical composition comprising a pharmaceutically inert carrier and an effective amount of a compound or a mixture of compounds of formula I:

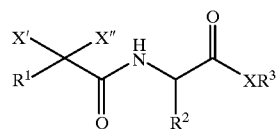

wherein $R^1$ is selected from the group consisting of
a) alkyl, alkenyl, alkcycloalkyl, phenyl—$(R)_m$—, naphthyl—$(R)_m$— wherein R is an alkylene group of from 1 to 8 carbon atoms and m is an integer equal to 0 or 1, cycloalkyl, and cycloalkenyl;
(b) a substituted phenyl group of formula II:

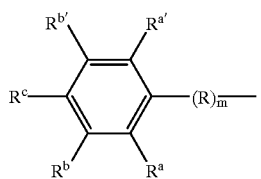

wherein R is alkylene of from 1 to 8 carbon atoms,
m is an integer equal to 0 or 1,
$R^a$ and $R^{a'}$ are independently selected from the group consisting of hydrogen, hydroxy, fluoro and methyl;
$R^b$ and $R^{b'}$ are independently selected from the group consisting of hydrogen, alkyl, alkoxy, aryl, cyano, cycloalkyl, halo, heteroaryl, heterocyclic, nitro, trihalomethyl, thioalkoxy, thioaryloxy, thioheteroaryloxy, and —$C(O)R^4$ where $R^4$ is selected from the group consisting of alkyl, aryl, alkoxy and aryloxy; and
$R^c$ is selected from the group consisting of hydrogen, alkyl, aryl, cyano, halo, nitro, and where $R^b$ and $R^c$ are fused to form a methylenedioxy ring with the phenyl ring; and
when $R^b$ and/or $R^{b'}$ and/or $R^c$ is fluoro, chloro, bromo and/or nitro, then $R^a$ and/or $R^{a'}$ can also be chloro; and
(c) 1- or 2-naphthyl—$(R)_m$— substituted at the 5, 6, 7 and/or 8 positions with 1 to 4 substituents selected from the group consisting alkyl, alkoxy, halo, cyano, nitro, trihalomethyl, and thioalkoxy wherein R is an alkylene group of from 1 to 8 carbon atoms and m is an integer equal to 0 or 1;
$R^2$ is selected from the group consisting of hydrogen, alkyl, phenyl, alkylalkoxy, alkylthioalkoxy; and
$R^3$ is selected from the group consisting of —$(CH_2)_n$ $CR^{10}R^5R^6$ wherein n is an integer equal to 0, 1 or 2, $R^5$ and $R^6$ are independently selected from hydrogen, alkyl, alkenyl, aryl, heteroaryl, heterocyclic, —$NR^7R^8$ where $R^7$ and $R^8$ are independently hydrogen or alkyl and —$COOR^9$ where $R^9$ is alkyl, and further wherein $R^5$ and $R^6$ can be joined to form a cycloalkyl group, a cycloalkenyl group, an aryl group, a heteroaryl group, and a heterocyclic group, and when $R^5$ and $R^6$ do not join to form an aryl or heteroaryl group, then $R^{10}$ is selected from hydrogen and alkyl with the proviso that when n is zero, then $R^{10}$ is hydrogen and when n is greater than zero and $R^5$ and $R^6$ are joined to form an aryl or heteroaryl group, then $R^{10}$ becomes a bond within that group;
X is oxygen or sulfur;

X' is hydrogen, hydroxy or fluoro;
X" is hydrogen, hydroxy or fluoro, or X' and X" together form an oxo group, and pharmaceutically acceptable salts thereof
with the provisos that:
when $R^1$ is phenyl, $R^2$ is —$CH(CH_3)CH_2CH_3$, X is oxygen, and X' and X" are hydrogen, then $R^3$ is not —$CH_2CH_3$ or —$CH_2CH(CH_3)_2$
when $R^1$ is phenyl, $R^3$ is —$CH_2CH(CH_3)_2$, X is oxygen, and X' and X" are hydrogen, then $R^2$ is not —CH$(CH_3)_2$
when $R^1$ is 3,5-di(trifluoromethyl)phenyl, $R^2$ is methyl, X is oxygen, and X' and X" are hydrogen, then $R^3$ is not —$CH_2CH(CH_3)_2$, and
when $R^1$ is —$CH_2$-phenyl, $R^3$ is —$CH_2CH_3$, X is oxygen, and X' and X" are hydrogen, then $R^2$ is not —$CH_2CH(CH_3)_2$.

4. The method according to claim 1, 2 or 3 wherein $R^1$ is an unsubstituted phenyl group.

5. The method according to claim 1, 2 or 3 wherein $R^1$ is an unsubstituted naphthyl group selected from the group consisting of 1-naphthyl and 2-naphthyl.

6. The method according to claim 1, 2 or 3 wherein $R^1$ is a substituted phenyl group of formula II.

7. The method according to claim 6 wherein the substituted phenyl group is defined by the following:
(a) monosubstituted phenyls having a single substitution at the 2, 3 or 4 positions wherein each of the particular substituents is governed by the respective $R^a$, $R^b$ and $R^c$ groups;
(b) disubstituted phenyls having two substituents at the 2,3-positions, 2,4-positions, 2,5-positions, 2,6-positions, 3,4-positions, 3,5-positions or 3,6-positions wherein each of these substituents is governed by the respective $R^a$, $R^{a'}$, $R^b$, $R^{b'}$ and $R^c$ groups; and
(c) trisubstituted phenyls having three substituents at the 2,3,4-positions, 2,3,5-positions, 2,3,6-positions, 3,4,5-positions and 3,4,6-positions again wherein each of these substituents is governed by the respective $R^a$, $R^{a'}$, $R^b$, $R^{b'}$ and $R^c$ groups.

8. The method according to claim 7 wherein the substituted phenyl groups are selected from the group consisting of 4-fluorophenyl, 4-chlorophenyl, 4-bromophenyl, 4-nitrophenyl, 4-methylphenyl, 3-methoxy-phenyl, 3-nitrophenyl, 3-fluorophenyl, 3-chlorophenyl, 3-bromophenyl, 3-thiomethoxyphenyl, 3-methylphenyl, 3-trifluoromethylphenyl, 2-hydroxyphenyl, 2-methylphenyl, 2-fluorophenyl, 3,4-dichlorophenyl, 3,4-methylenedioxyphenyl, 3,5-difluorophenyl, 3,5-dichlorophenyl, 2,4-dichlorophenyl, and 2,5-difluorophenyl.

9. The method according to claim 1, 2 or 3 wherein $R^1$ is a phenyl—$(R)_m$-group where R is alkylene of from 1 to 8 carbon atoms and m is equal to 1.

10. The method according to claim 9 wherein $R^1$ is selected from the group consisting of benzyl, 3-phenyl-n-propyl and 4-phenyl-n-butyl.

11. The method according to claim 1, 2 or 3 wherein $R^1$ is selected from the group consisting of alkyl, alkenyl, alkcycloalkyl, cycloalkyl and cycloalkenyl groups.

12. The method according to claim 11 wherein $R^1$ is alkyl.

13. The method according to claim 11 wherein $R^1$ is cycloalkyl.

14. The method according to claim 11 wherein $R^1$ is alkenyl.

15. The method according to claim 11 wherein $R^1$ is cycloalkenyl.

16. The method according to claim 11 wherein the $R^1$ alkyl, cycloalkyl, alkcycloalkyl, alkenyl and cycloalkenyl groups are selected from the group consisting of sec-butyl, cyclopropyl, cyclobutyl, cyclohexyl, cyclopentyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, and —CH$_2$CH$_2$-cyclopentyl.

17. The method according to claim 1, 2 or 3 wherein R$^2$ is selected from the group consisting of alkyl of from 1 to 4 carbon atoms, alkylalkoxy of from 1 to 4 carbon atoms, phenyl and alkylthioalkoxy of from 1 to 4 carbon atoms.

18. The method according to claim 9 wherein R$^2$ is selected from the group consisting of methyl, ethyl, n-propyl, iso-propyl, n-butyl, iso-butyl, —CH$_2$CH$_2$SCH$_3$ and phenyl.

19. The method according to claim 1, 2 or 3 wherein X' and X" are both hydrogen and X is oxygen.

20. The method according to claim 19 wherein R$^3$ is selected from the group consisting of methyl, ethyl, iso-propyl, n-propyl, n-butyl, iso-butyl, cyclopentyl, allyl, iso-but-2-enyl, 3-methylpentyl, —CH$_2$-cyclopropyl, —CH$_2$-cyclohexyl, —CH$_2$-(3-tetrahydrofuranyl), —CH$_2$-thien-2-yl, —CH$_2$(1-methyl)cyclopropyl, —CH$_2$-thien-3-yl, —CH$_2$—C(O)O-tert-butyl, —CH$_2$—C(CH$_3$)$_3$, —CH$_2$CH(CH$_2$CH$_3$)$_2$, -2-methylcyclopentyl, -cyclohex-2enyl, —CH[CH(CH$_3$)$_2$]COOCH$_3$, —CH$_2$CH$_2$N(CH$_3$)$_2$, —CH$_2$C(CH$_3$)=CH$_2$, and —CH$_2$CH=C(CH$_3$)$_2$.

21. The method according to claim 1, 2 or 3 wherein X' and X" are both hydrogen and X is sulfur.

22. The method according to claim 19 wherein R$^3$ is selected from the group consisting of iso-but-2-enyl and iso-butyl.

23. The method according to claims 1, 2 or 3 wherein the compound of formula I is selected from the group consisting of:

N-(phenylacetyl)alanine iso-butyl ester
N-(3-phenylpropionyl)alanine iso-butyl ester
N-(3-methylpentanoyl)alanine iso-butyl ester
N-[(4-chlorophenyl)acetyl]alanine iso-butyl ester
N-[(3,4-dichlorophenyl)acetyl]alanine iso-butyl ester
N-[(1-naphthyl)acetyl]alanine iso-butyl ester
N-[(2-naphthyl)acetyl]alanine iso-butyl ester
N-(4-phenylbutanoyl)alanine iso-butyl ester
N-(5-phenylpentanoyl)alanine iso-butyl ester
2-[(3,4-dichlorophenyl)acetamido]butyric acid iso-butyl ester
2-[(3-methoxyphenyl)acetamido]butyric acid iso-butyl ester
2-[(4-nitrophenyl)acetamido]butyric acid iso-butyl ester
2-[(3,4-methylenedioxyphenyl)acetamido]butyric acid iso-butyl ester
2-[(4-chlorophenyl)acetamido]butyric acid iso-butyl ester
2-[(3-nitrophenyl)acetamido]butyric acid iso-butyl ester
2-[(2-hydroxyphenyl)acetamido]butyric acid iso-butyl ester
2-[(2-naphthyl)acetamido]butyric acid iso-butyl ester
2-[(2,4-dichlorophenyl)acetamido]butyric acid iso-butyl ester
2-[(4-bromophenyl)acetamido]butyric acid iso-butyl ester
2-[(3-chlorophenyl)acetamido])butyric acid iso-butyl ester
2-[(3-fluorophenyl)acetamido]butyric acid iso-butyl ester
2-[(2-methylphenyl)acetamido]butyric acid iso-butyl ester
2-[(2-fluorophenyl)acetamido]butyric acid iso-butyl ester
2-[(4-fluorophenyl)acetamido]butyric acid iso-butyl ester
2-[(3-bromophenyl)acetamido]butyric acid iso-butyl ester
2-[(3-trifluoromethylphenyl)acetamido]butyric acid iso-butyl ester
2-(phenylacetamido)butyric acid iso-butyl ester
N-(phenylacetyl)valine 2-methylbutyl ester
N-(phenylacetyl)methionine iso-butyl ester
N-(phenylacetyl)leucine iso-butyl ester
N-[(3-chlorophenyl)acetyl]alanine 3-methylbut-2-enyl ester
N-[(3-chlorophenyl)acetyl]alanine cyclopropylmethyl ester
N-[(3-chlorophenyl)acetyl]alanine 2-thienylmethyl ester
N-[(3-chlorophenyl)acetyl]alanine (1-methylcyclopropyl) methyl ester
N-[(3-chlorophenyl)acetyl]alanine 3-thienylmethyl ester
N-[(3-chlorophenyl)acetyl]alanine 2-methylcyclopentyl ester
N-[(3-chlorophenyl)acetyl]alanine 2-methylprop-2-enyl ester
N-[(3-chlorophenyl)acetyl]alanine cyclohex-2-enyl ester
N-[(3-methylthiophenyl)acetyl]alanine iso-butyl ester
N-[(3-methylphenyl)acetyl]alanine iso-butyl ester
N-[(2,5-difluorophenyl)acetyl]alanine iso-butyl ester
N-[(3,5-diflurophenyl)acetyl]alanine iso-butyl ester
N-[(3-thienyl)acetyl]alanine iso-butyl ester
N-[(4-methylphenyl)acetyl]alanine iso-butyl ester
N-(phenylacetyl)alanine (1-methoxycarbonyl)iso-butyl ester
N-[(3-nitrophenyl)acetyl]alanine iso-butyl ester
N-[(3,5-difluorophenyl)acetyl]alanine ethyl ester
N-[(3-nitrophenyl)acetyl]methionine ethyl ester
N-[(3-chlorophenyl)acetyl]alanine iso-butyl ester
N-[(3-chlorophenyl)acetyl]alanine 2-(N,N-dimethylamino) ethyl ester
2-[(3,5-dichlorophenyl)acetamido]hexanoic acid methyl ester
N-[(3,5-dichlorophenyl)acetyl]alanine iso-butyl ester
N-(cyclohexylacetyl)alanine iso-butyl ester
N-(cyclopentylacetyl)alanine iso-butyl ester
N-[(cyclohex-1-enyl)acetyl]alanine iso-butyl ester
N-[(3-chlorophenyl)acetyl]alanine 3-methylbut-2-enyl thioester
N-[(2-phenyl)-2-fluoroacetyl]alanine ethyl ester
N-(3,5-difluorophenylacetyl)phenylglycine methyl ester
N-(3,5-difluorophenylacetyl)phenylglycine iso-butyl ester
N-(cyclopentylacetyl)phenylglycine methyl ester
N-(cyclopentylacetyl)alanine methyl ester
N-(cyclopropylacetyl)phenylglycine methyl ester
N-(cyclopropylacetyl)alanine methyl ester; and
N-[(3-nitrophenyl)acetyl]methionine iso-butyl ester.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 43 amino acids
       (B) TYPE: amino acid
       (D) TOPOLOGY: linear (ii) MOLECULE TYPE: peptide (xi) SEQUENCE DESCRIPTION: SEQ ID NO:1:

```
Asp Ala Glu Phe Arg His Asp Ser Gly Tyr Glu Val His His
1               5                   10
Gln Lys Leu Val Phe Phe Ala Glu Asp Val Gly Ser Asn Lys
15                  20                  25
Gly Ala Ile Ile Gly Leu Met Val Gly Gly Val Val Ile Ala
        30                  35                  40
Thr
```